US006683048B1

(12) United States Patent
Blaschuk et al.

(10) Patent No.: US 6,683,048 B1
(45) Date of Patent: Jan. 27, 2004

(54) COMPOUNDS AND METHODS FOR STIMULATING GENE EXPRESSION AND CELLULAR DIFFERENTIATION

(75) Inventors: Orest W. Blaschuk, Westmount (CA); Barbara J. Gour, Montreal (CA)

(73) Assignee: McGill University, Quebec (CA)

( * ) Notice: Subject to any disclaimer, the term of this patent is extended or adjusted under 35 U.S.C. 154(b) by 0 days.

(21) Appl. No.: 09/265,107

(22) Filed: Mar. 9, 1999

Related U.S. Application Data

(63) Continuation-in-part of application No. 09/057,363, filed on Apr. 8, 1998.

(60) Provisional application No. 60/043,361, filed on Apr. 10, 1997.

(51) Int. Cl.$^7$ .......................... A61K 38/08; C07K 5/06

(52) U.S. Cl. ................................ 514/2; 514/9; 514/11; 514/12; 514/13; 514/14; 514/15; 514/16; 514/17; 530/300; 530/326; 530/328; 530/329; 530/330

(58) Field of Search ........................... 514/9, 2, 12, 11, 514/13, 14, 15, 16, 17; 530/328, 326, 329, 330, 300

(56) References Cited

U.S. PATENT DOCUMENTS 5,972,884 A * 10/1999 Cohen et al. ................. 514/12

FOREIGN PATENT DOCUMENTS

WO WO 98/42296 10/1998
WO WO 98/45319 10/1998

OTHER PUBLICATIONS

Bullions et al., "The role of beta–catenin in cell adhesion, signal transduction, and cancer," *Current Opinion in Oncology 10*(1): 81–87, 1998.

Gat et al., "De Novo Hair Follicle Morphogenesis and Hair Tumors in Mice Expressing a Truncated β–Catenin in Skin," *Cell 95*: 605–614, 1998.

Nagahara et al., "Transduction of full–length TAT fusion proteins into mammalian cells: TAT–p27$^{Kip1}$ induces cell migration," *Nature Medicine 4*(12): 1449–1452, 1998.

Oro and Scott, "Splitting Hairs: Dissecting Roles of Signaling Systems in Epidermal Development," *Cell 95*: 575–578, 1998.

Willert and Roel Nusse, "β–catenin: a key mediator of Wnt signaling," *Current Opinions in Genetics & Development 8*: 95–102, 1998.

* cited by examiner

*Primary Examiner*—Christopher S. F. Low
*Assistant Examiner*—Chih-Min Kam
(74) *Attorney, Agent, or Firm*—Seed IP Law Group PLLC

(57) ABSTRACT

Modulating agents for inhibiting an interaction between α-catenin and β-catenin are provided. The modulating agents comprise one or more of: (a) a β-catenin HAV motif; (b) a peptide analogue or mimetic of a β-catenin HAV motif; or (c) an antibody or antigen-binding fragment thereof that specifically binds to a β-catenin HAV motif. Methods for using such modulating agents for inhibiting cadherin-mediated cell adhesion in a variety of contexts are also provided.

16 Claims, 8 Drawing Sheets

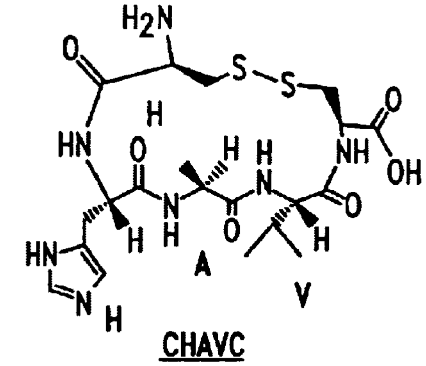
CHAVC
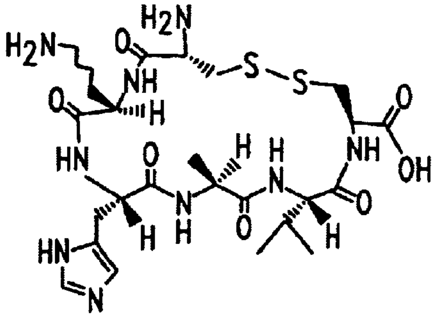
CKHAVC
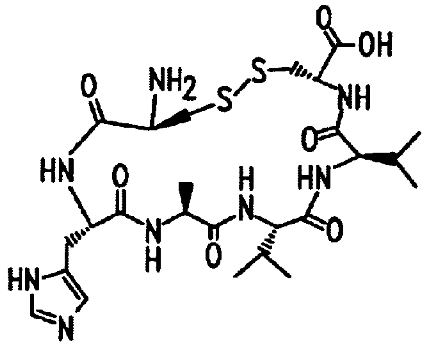
CHAVVC
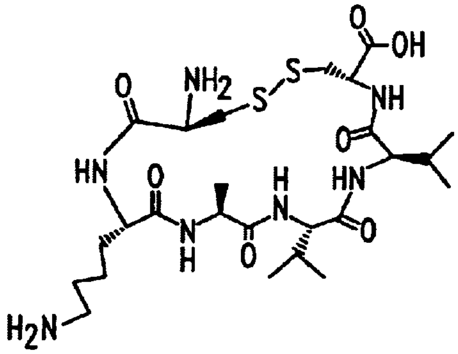
CKAVVC
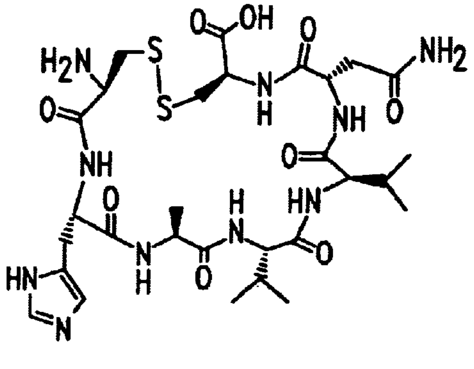
CHAVVNC
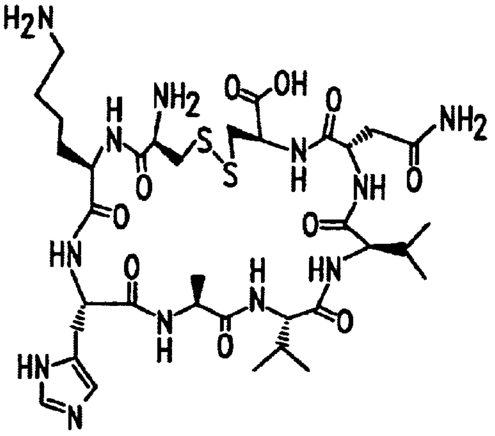
CKHAVVNC
*Fig. 2A*

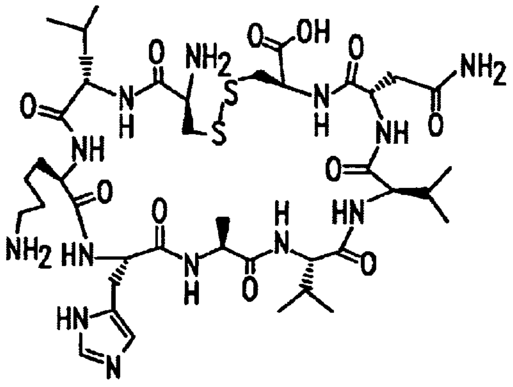
CLKHAVVNC
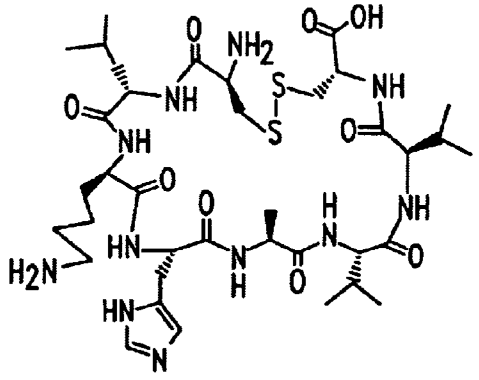
CLKHAVVC
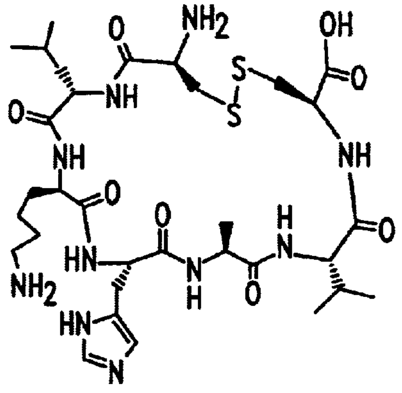
CLKHAVC
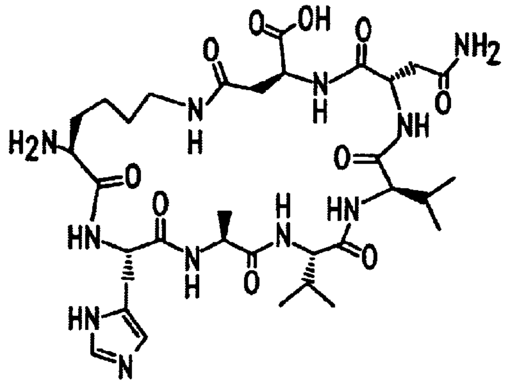
KHAVVND
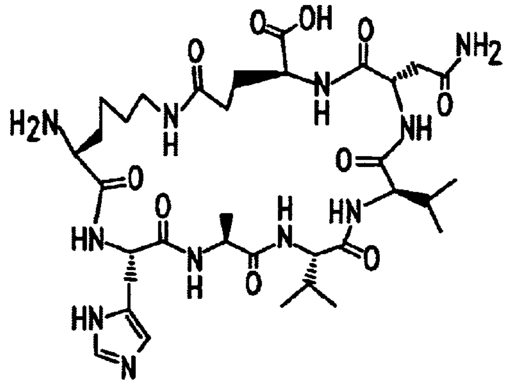
KHAVVNE
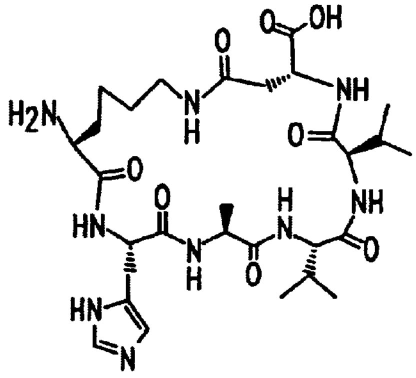
KHAVVD
*Fig. 2B*

KHAVVE

```
hum N-cad      LRAHAVDINGNQVENPIDIVINVIDMNDNRPEFLHQVWN.GTVP
mouse N-cad    LRAHAVDINGNQVENPIDIVINVIDMNDNRPEFLHQVWN.GSVP
cow N-cad      LRAHAVDINGNQVENPIDIVINVIDMNDNRPEFLHQVWN.GTVP
chick N-cad    LRAHAVDVNGNQVENPIDIVINVIDMNDNRPEFLHQVWN.GTVP
hum P-cad      LFGHAVSENGASVEDPMNISIIVTDQNDHKPKFTQDTF.RGSVL
mouse P-cad    LYGHAVSENGASVEEPMNISIIVTDQNDNKPKFTQDTF.RGSVL
hum E-cad      LFSHAVSSNGNAVEDPMEILITVTDQNDNKPEFTQEVF.KGSVM
chick L-cam    LLSHAVSASGQPVEDPMEIIITVMDQNDNKPVFIKEVFV.GYIE
mouse E-cad    LYSHAVSSNGEAVEDPMEIVITVTDQNDNRPEFTQEVFE.GSVA
frog XT-cad    LFSHAVSSNGANVEDPMEIIIKVQDQNDNDPVFTQSVFE.GSVP
frog XB-cad    LLSHAVSENGASVEEPMEITVTVIDQNDNRPKFTQPVF.RGSVR
frog EP-cad    LSSHAVSENGSPVEEPMEITINVIDQNDNRPKFTQDVF.RGSVR
chick B-cad    LYSHAVSENGKPVEEPMEIIVTVTDQNDNKPQFTQEVF.RGSVP
chick R-cad    LRAHAVDMNGNKVENPIDLYIYVIDMNDNRPEFINQVYN.GSVD

fruit fly cat  MLKHAVVNLINYQDDAELATRAIPELIKLLNDEDQVVVSQAAMM
hum cat        MLKHAVVNLINYQDDAELATRAIPELTKLLNDEDQVVVNKAAVM
frog cat       MLKHAVVNLINYQDDAELATRAIPELTKLLNDEDQVVVNKAAVM
worm cat       MLKHAVVNLINYQDDADLATRAIPELTKLLNDEDQVVVSQAAMM
mouse cat      MLKHAVVNLINYQDDAELATRAIPELTKLLNDEDQVVVNKAAVM
sea urch cat   MLKHAVVNLINYQDDADLATRAIPELTKLLNDDDLVVVNQAAVM

consensus      ll HAV e  n  edp   t tv dm     e  q v nkgsvm
               m      n     d a     ai el     d        aa
```

Fig. 4

SEQUENCE LISTING

<160> NUMBER OF SEQ ID NOS: 75

<210> SEQ ID NO 1
<211> LENGTH: 5
<212> TYPE: PRT
<213> ORGANISM: Artificial Sequence
<220> FEATURE:
<223> OTHER INFORMATION: Modulating agent comprising beta-catenin HAV motif

<400> SEQUENCE: 1

Lys His Ala Val Val
1 5

<210> SEQ ID NO 2
<211> LENGTH: 5
<212> TYPE: PRT
<213> ORGANISM: Unknown
<220> FEATURE:
<223> OTHER INFORMATION: Calcium binding motif of a classical cadherin protein
<220> FEATURE:
<221> NAME/KEY: VARIANT
<222> LOCATION: (1)...(5)
<223> OTHER INFORMATION: Xaa = any amino acid

<400> SEQUENCE: 2

Asp Xaa Asn Asp Asn
1 5

<210> SEQ ID NO 3
<211> LENGTH: 4
<212> TYPE: PRT
<213> ORGANISM: Unknown
<220> FEATURE:
<223> OTHER INFORMATION: Calcium binding motif for a classical cadherin protein

<400> SEQUENCE: 3

Leu Asp Arg Glu
1

<210> SEQ ID NO 4
<211> LENGTH: 8
<212> TYPE: PRT
<213> ORGANISM: Artificial Sequence
<220> FEATURE:
<223> OTHER INFORMATION: Cyclic Modulating Agent comprising beta-catenin HAV motif

<400> SEQUENCE: 4

Cys Lys His Ala Val Val Asn Cys
1 5

<210> SEQ ID NO 5
<211> LENGTH: 8
<212> TYPE: PRT
<213> ORGANISM: Artificial Sequence
<220> FEATURE:
<223> OTHER INFORMATION: Cyclic Modulating Agent comprising a beta-catenin HAV motif

<400> SEQUENCE: 5

Cys Lys His Ala Val Val Asn Cys
1 5

-continued

<210> SEQ ID NO 6
<211> LENGTH: 8
<212> TYPE: PRT
<213> ORGANISM: Artificial Sequence
<220> FEATURE:
<223> OTHER INFORMATION: Control Peptide

<400> SEQUENCE: 6

Cys Lys His Gly Val Val Asn Cys
1 5

<210> SEQ ID NO 7
<211> LENGTH: 10
<212> TYPE: PRT
<213> ORGANISM: Unknown
<220> FEATURE:
<223> OTHER INFORMATION: Partial beta-catenin sequence with HAV motif and flanking residues

<400> SEQUENCE: 7

Leu Lys His Ala Val Val Asn Leu Ile Asn
1 5 10

<210> SEQ ID NO 8
<211> LENGTH: 6
<212> TYPE: PRT
<213> ORGANISM: Artificial Sequence
<220> FEATURE:
<223> OTHER INFORMATION: Linear peptide modulating agent

<400> SEQUENCE: 8

Lys His Ala Val Val Asn
1 5

<210> SEQ ID NO 9
<211> LENGTH: 7
<212> TYPE: PRT
<213> ORGANISM: Artificial Sequence
<220> FEATURE:
<223> OTHER INFORMATION: Linear peptide modulating agent

<400> SEQUENCE: 9

Leu Lys His Ala Val Val Asn
1 5

<210> SEQ ID NO 10
<211> LENGTH: 6
<212> TYPE: PRT
<213> ORGANISM: Artificial Sequence
<220> FEATURE:
<223> OTHER INFORMATION: Linear peptide modulating agent

<400> SEQUENCE: 10

Leu Lys His Ala Val Val
1 5

<210> SEQ ID NO 11
<211> LENGTH: 5
<212> TYPE: PRT
<213> ORGANISM: Artificial Sequence
<220> FEATURE:
<223> OTHER INFORMATION: Linear peptide modulating agent

<400> SEQUENCE: 11

Leu Lys His Ala Val
1 5

-continued

<210> SEQ ID NO 12
<211> LENGTH: 9
<212> TYPE: PRT
<213> ORGANISM: Artificial Sequence
<220> FEATURE:
<223> OTHER INFORMATION: Linear peptide modulating agent

<400> SEQUENCE: 12

Cys Leu Lys His Ala Val Val Asn Cys
 1               5

<210> SEQ ID NO 13
<211> LENGTH: 8
<212> TYPE: PRT
<213> ORGANISM: Artificial Sequence
<220> FEATURE:
<223> OTHER INFORMATION: Linear peptide modulating agent

<400> SEQUENCE: 13

Cys Leu Lys His Ala Val Val Cys
 1               5

<210> SEQ ID NO 14
<211> LENGTH: 7
<212> TYPE: PRT
<213> ORGANISM: Artificial Sequence
<220> FEATURE:
<223> OTHER INFORMATION: Linear peptide modulating agent

<400> SEQUENCE: 14

Cys Leu Lys His Ala Val Cys
 1               5

<210> SEQ ID NO 15
<211> LENGTH: 7
<212> TYPE: PRT
<213> ORGANISM: Artificial Sequence
<220> FEATURE:
<223> OTHER INFORMATION: Linear peptide modulating agent

<400> SEQUENCE: 15

Cys Lys His Ala Val Val Cys
 1               5

<210> SEQ ID NO 16
<211> LENGTH: 4
<212> TYPE: PRT
<213> ORGANISM: Artificial Sequence
<220> FEATURE:
<223> OTHER INFORMATION: Linear peptide modulating agent

<400> SEQUENCE: 16

Lys His Ala Val
 1

<210> SEQ ID NO 17
<211> LENGTH: 5
<212> TYPE: PRT
<213> ORGANISM: Artificial Sequence
<220> FEATURE:
<223> OTHER INFORMATION: Linear peptide modulating agent

<400> SEQUENCE: 17

His Ala Val Val Asn
 1               5

<210> SEQ ID NO 18

-continued

```
<211> LENGTH: 4
<212> TYPE: PRT
<213> ORGANISM: Artificial Sequence
<220> FEATURE:
<223> OTHER INFORMATION: Linear peptide modulating agent

<400> SEQUENCE: 18

His Ala Val Asn
 1


<210> SEQ ID NO 19
<211> LENGTH: 6
<212> TYPE: PRT
<213> ORGANISM: Artificial Sequence
<220> FEATURE:
<223> OTHER INFORMATION: Linear peptide modulating agent

<400> SEQUENCE: 19

Cys Lys His Ala Val Cys
 1               5


<210> SEQ ID NO 20
<211> LENGTH: 7
<212> TYPE: PRT
<213> ORGANISM: Artificial Sequence
<220> FEATURE:
<223> OTHER INFORMATION: Linear peptide modulating agent

<400> SEQUENCE: 20

Cys His Ala Val Val Asn Cys
 1               5


<210> SEQ ID NO 21
<211> LENGTH: 6
<212> TYPE: PRT
<213> ORGANISM: Artificial Sequence
<220> FEATURE:
<223> OTHER INFORMATION: Linear peptide modulating agent

<400> SEQUENCE: 21

Cys His Ala Val Val Cys
 1               5


<210> SEQ ID NO 22
<211> LENGTH: 5
<212> TYPE: PRT
<213> ORGANISM: Artificial Sequence
<220> FEATURE:
<223> OTHER INFORMATION: Linear peptide modulating agent

<400> SEQUENCE: 22

Cys His Ala Val Cys
 1               5


<210> SEQ ID NO 23
<211> LENGTH: 9
<212> TYPE: PRT
<213> ORGANISM: Artificial Sequence
<220> FEATURE:
<223> OTHER INFORMATION: Cyclic modulating agent comprising a
      beta-catenin HAV motif

<400> SEQUENCE: 23

Cys Leu Lys His Ala Val Val Asn Cys
 1               5


<210> SEQ ID NO 24
```

-continued

```
<211> LENGTH: 8
<212> TYPE: PRT
<213> ORGANISM: Artificial Sequence
<220> FEATURE:
<223> OTHER INFORMATION: Cyclic modulating agent comprising a
      beta-catenin HAV motif

<400> SEQUENCE: 24

Cys Leu Lys His Ala Val Val Cys
 1               5


<210> SEQ ID NO 25
<211> LENGTH: 7
<212> TYPE: PRT
<213> ORGANISM: Artificial Sequence
<220> FEATURE:
<223> OTHER INFORMATION: Cyclic modulating agent comprising a
      beta-catenin HAV motif

<400> SEQUENCE: 25

Cys Lys His Ala Val Val Cys
 1               5


<210> SEQ ID NO 26
<211> LENGTH: 7
<212> TYPE: PRT
<213> ORGANISM: Artificial Sequence
<220> FEATURE:
<223> OTHER INFORMATION: Cyclic modulating agent comprising a
      beta-catenin HAV motif

<400> SEQUENCE: 26

Lys His Ala Val Val Asn Asp
 1               5


<210> SEQ ID NO 27
<211> LENGTH: 7
<212> TYPE: PRT
<213> ORGANISM: Artificial Sequence
<220> FEATURE:
<223> OTHER INFORMATION: Cyclic modulating agent comprising a beta-catenin
      HAV motif

<400> SEQUENCE: 27

Lys His Ala Val Val Asn Glu
 1               5


<210> SEQ ID NO 28
<211> LENGTH: 6
<212> TYPE: PRT
<213> ORGANISM: Artificial Sequence
<220> FEATURE:
<223> OTHER INFORMATION: Cyclic modulating agent comprising a
      beta-catenin HAV motif

<400> SEQUENCE: 28

Lys His Ala Val Val Asp
 1               5


<210> SEQ ID NO 29
<211> LENGTH: 6
<212> TYPE: PRT
<213> ORGANISM: Artificial Sequence
<220> FEATURE:
<223> OTHER INFORMATION: Cyclic modulating agent comprising a
      beta-catenin HAV motif

<400> SEQUENCE: 29
```

-continued

```
Lys His Ala Val Val Glu
 1              5


<210> SEQ ID NO 30
<211> LENGTH: 7
<212> TYPE: PRT
<213> ORGANISM: Artificial Sequence
<220> FEATURE:
<223> OTHER INFORMATION: Cyclic modulating agent comprising a
      beta-catenin HAV motif

<400> SEQUENCE: 30

Cys Leu Lys His Ala Val Cys
 1              5


<210> SEQ ID NO 31
<211> LENGTH: 6
<212> TYPE: PRT
<213> ORGANISM: Artificial Sequence
<220> FEATURE:
<223> OTHER INFORMATION: Cyclic modulating agent comprising a
      beta-catenin HAV motif

<400> SEQUENCE: 31

Cys Lys His Ala Val Cys
 1              5


<210> SEQ ID NO 32
<211> LENGTH: 7
<212> TYPE: PRT
<213> ORGANISM: Artificial Sequence
<220> FEATURE:
<223> OTHER INFORMATION: Cyclic modulating agent comprising a
      beta-catenin HAV motif

<400> SEQUENCE: 32

Cys His Ala Val Val Asn Cys
 1              5


<210> SEQ ID NO 33
<211> LENGTH: 6
<212> TYPE: PRT
<213> ORGANISM: Artificial Sequence
<220> FEATURE:
<223> OTHER INFORMATION: Cyclic modulating agent comprising a
      beta-catenin HAV motif

<400> SEQUENCE: 33

Cys His Ala Val Val Cys
 1              5


<210> SEQ ID NO 34
<211> LENGTH: 5
<212> TYPE: PRT
<213> ORGANISM: Artificial Sequence
<220> FEATURE:
<223> OTHER INFORMATION: Cyclic modulating agent comprising a
      beta-catenin HAV motif

<400> SEQUENCE: 34

Cys His Ala Val Cys
 1              5


<210> SEQ ID NO 35
<211> LENGTH: 5
<212> TYPE: PRT
<213> ORGANISM: Artificial Sequence
<220> FEATURE:
```

-continued

<223> OTHER INFORMATION: Cyclic modulating agent comprising a beta-catenin HAV motif

<400> SEQUENCE: 35

Lys His Ala Val Asp
1 5

<210> SEQ ID NO 36
<211> LENGTH: 5
<212> TYPE: PRT
<213> ORGANISM: Artificial Sequence
<220> FEATURE:
<223> OTHER INFORMATION: Cyclic modulating agent comprising a beta-catenin HAV motif

<400> SEQUENCE: 36

Lys His Ala Val Glu
1 5

<210> SEQ ID NO 37
<211> LENGTH: 6
<212> TYPE: PRT
<213> ORGANISM: Artificial Sequence
<220> FEATURE:
<223> OTHER INFORMATION: Cyclic modulating agent comprising a beta-catenin HAV motif

<400> SEQUENCE: 37

Lys His Ala Val Val Asn
1 5

<210> SEQ ID NO 38
<211> LENGTH: 7
<212> TYPE: PRT
<213> ORGANISM: Artificial Sequence
<220> FEATURE:
<223> OTHER INFORMATION: Cyclic modulating agent comprising a beta-catenin HAV motif

<400> SEQUENCE: 38

Leu Lys His Ala Val Val Asn
1 5

<210> SEQ ID NO 39
<211> LENGTH: 5
<212> TYPE: PRT
<213> ORGANISM: Artificial Sequence
<220> FEATURE:
<223> OTHER INFORMATION: Cyclic modulating agent comprising a beta-catenin HAV motif

<400> SEQUENCE: 39

His Ala Val Val Asn
1 5

<210> SEQ ID NO 40
<211> LENGTH: 4
<212> TYPE: PRT
<213> ORGANISM: Artificial Sequence
<220> FEATURE:
<223> OTHER INFORMATION: Cyclic modulating agent comprising a beta-catenin HAV motif

<400> SEQUENCE: 40

His Ala Val Val
1

-continued

<210> SEQ ID NO 41
<211> LENGTH: 8
<212> TYPE: PRT
<213> ORGANISM: Artificial Sequence
<220> FEATURE:
<223> OTHER INFORMATION: Cyclic modulating agent comprising a
beta-catenin HAV motif
<220> FEATURE:
<221> NAME/KEY: MOD_RES
<222> LOCATION: (8)...(8)
<223> OTHER INFORMATION: Where Xaa is beta,beta-dimethyl cysteine

<400> SEQUENCE: 41

Cys Lys His Ala Val Val Asn Xaa
1 5

<210> SEQ ID NO 42
<211> LENGTH: 8
<212> TYPE: PRT
<213> ORGANISM: Artificial Sequence
<220> FEATURE:
<223> OTHER INFORMATION: Cyclic modulating agent comprising a
beta-catenin HAV motif
<220> FEATURE:
<221> NAME/KEY: MOD_RES
<222> LOCATION: (1)...(1)
<223> OTHER INFORMATION: Where Xaa is beta,beta-tetramethylene cysteine

<400> SEQUENCE: 42

Xaa Lys His Ala Val Val Asn Cys
1 5

<210> SEQ ID NO 43
<211> LENGTH: 8
<212> TYPE: PRT
<213> ORGANISM: Artificial Sequence
<220> FEATURE:
<223> OTHER INFORMATION: Cyclic modulating agent comprising a
beta-catenin HAV motif
<220> FEATURE:
<221> NAME/KEY: MOD_RES
<222> LOCATION: (0)...(0)
<223> OTHER INFORMATION: Where Xaa is beta,beta-pentamethylene cysteine

<400> SEQUENCE: 43

Xaa Lys His Ala Val Val Asn Cys
1 5

<210> SEQ ID NO 44
<211> LENGTH: 8
<212> TYPE: PRT
<213> ORGANISM: Artificial Sequence
<220> FEATURE:
<223> OTHER INFORMATION: Cyclic modulating agent comprising a
beta-catenin HAV motif
<220> FEATURE:
<221> NAME/KEY: MOD_RES
<222> LOCATION: (1)...(1)
<223> OTHER INFORMATION: Where Xaa is beta-mercaptopropionic acid

<400> SEQUENCE: 44

Xaa Lys His Ala Val Val Asn Cys
1 5

<210> SEQ ID NO 45
<211> LENGTH: 8
<212> TYPE: PRT
<213> ORGANISM: Artificial Sequence
<220> FEATURE:
<223> OTHER INFORMATION: Cyclic modulating agent comprising a
beta-catenin HAV motif -continued <220> FEATURE:
<221> NAME/KEY: MOD_RES
<222> LOCATION: (1)...(1)
<223> OTHER INFORMATION: Where Xaa is beta,beta-pentamethylene-beta-
      mercaptopropionic acid

<400> SEQUENCE: 45

```
Xaa Lys His Ala Val Val Asn Cys
 1               5
```

<210> SEQ ID NO 46
<211> LENGTH: 4
<212> TYPE: PRT
<213> ORGANISM: Artificial Sequence
<220> FEATURE:
<223> OTHER INFORMATION: Synthesized cyclic peptide

<400> SEQUENCE: 46

```
Trp Gly Gly Trp
 1
```

<210> SEQ ID NO 47
<211> LENGTH: 16
<212> TYPE: PRT
<213> ORGANISM: Drosophila melanogaster

<400> SEQUENCE: 47

```
Arg Gln Ile Lys Ile Trp Phe Gln Asn Arg Arg Met Lys Trp Lys Lys
 1               5                  10                  15
```

<210> SEQ ID NO 48
<211> LENGTH: 16
<212> TYPE: PRT
<213> ORGANISM: Drosophila melanogaster

<400> SEQUENCE: 48

```
Arg Gln Ile Lys Ile Trp Pro Gln Asn Arg Arg Asn Lys Trp Lys Lys
 1               5                  10                  15
```

<210> SEQ ID NO 49
<211> LENGTH: 16
<212> TYPE: PRT
<213> ORGANISM: Artificial Sequence
<220> FEATURE:
<223> OTHER INFORMATION: Analogue of 16 amino acid internalization
      Sequence of Drosophila antennapedia protein

<400> SEQUENCE: 49

```
Lys Lys Trp Lys Lys Trp Trp Lys Lys Trp Trp Lys Lys Trp Lys Lys
 1               5                  10                  15
```

<210> SEQ ID NO 50
<211> LENGTH: 22
<212> TYPE: PRT
<213> ORGANISM: Artificial Sequence
<220> FEATURE:
<223> OTHER INFORMATION: Modulating agent comprising beta-catenin HAV
      motif and a covalently linked Antennapedia internalization
      sequence

<400> SEQUENCE: 50

```
Lys His Ala Val Val Asn Arg Gln Ile Lys Ile Trp Phe Gln Asn Arg
 1               5                  10                  15

Arg Met Lys Trp Lys Lys
            20
```

-continued

<210> SEQ ID NO 51
<211> LENGTH: 8
<212> TYPE: PRT
<213> ORGANISM: Artificial Sequence
<220> FEATURE:
<223> OTHER INFORMATION: Cyclic control peptide

<400> SEQUENCE: 51

Cys Lys His Gly Val Val Asn Cys
1 5

<210> SEQ ID NO 52
<211> LENGTH: 43
<212> TYPE: PRT
<213> ORGANISM: Homo sapien

<400> SEQUENCE: 52

Leu Arg Ala His Ala Val Asp Ile Asn Gly Asn Gln Val Glu Asn Pro
1 5 10 15

Ile Asp Ile Val Ile Asn Val Ile Asp Met Asn Asp Asn Arg Pro Glu
20 25 30

Phe Leu His Gln Val Trp Asn Gly Thr Val Pro
35 40

<210> SEQ ID NO 53
<211> LENGTH: 43
<212> TYPE: PRT
<213> ORGANISM: Mus musculus

<400> SEQUENCE: 53

Leu Arg Ala His Ala Val Asp Ile Asn Gly Asn Gln Val Glu Asn Pro
1 5 10 15

Ile Asp Ile Val Ile Asn Val Ile Asp Met Asn Asp Asn Arg Pro Glu
20 25 30

Phe Leu His Gln Val Trp Asn Gly Ser Val Pro
35 40

<210> SEQ ID NO 54
<211> LENGTH: 43
<212> TYPE: PRT
<213> ORGANISM: Bos torus

<400> SEQUENCE: 54

Leu Arg Ala His Ala Val Asp Ile Asn Gly Asn Gln Val Glu Asn Pro
1 5 10 15

Ile Asp Ile Val Ile Asn Val Ile Asp Met Asn Asp Asn Arg Pro Glu
20 25 30

Phe Leu His Gln Val Trp Asn Gly Thr Val Pro
35 40

<210> SEQ ID NO 55
<211> LENGTH: 43
<212> TYPE: PRT
<213> ORGANISM: Gallus gallus

<400> SEQUENCE: 55

Leu Arg Ala His Ala Val Asp Val Asn Gly Asn Gln Val Glu Asn Pro
1 5 10 15

Ile Asp Ile Val Ile Asn Val Ile Asp Met Asn Asp Asn Arg Pro Glu
20 25 30

Phe Leu His Gln Val Trp Asn Gly Thr Val Pro
35 40

-continued

<210> SEQ ID NO 56
<211> LENGTH: 43
<212> TYPE: PRT
<213> ORGANISM: Homo sapien

<400> SEQUENCE: 56

```
Leu Phe Gly His Ala Val Ser Glu Asn Gly Ala Ser Val Glu Asp Pro
 1               5                  10                  15

Met Asn Ile Ser Ile Ile Val Thr Asp Gln Asn Asp His Lys Pro Lys
            20                  25                  30

Phe Thr Gln Asp Thr Phe Arg Gly Ser Val Leu
        35                  40
```

<210> SEQ ID NO 57
<211> LENGTH: 43
<212> TYPE: PRT
<213> ORGANISM: Mus musculus

<400> SEQUENCE: 57

```
Leu Tyr Gly His Ala Val Ser Glu Asn Gly Ala Ser Val Glu Glu Pro
 1               5                  10                  15

Met Asn Ile Ser Ile Ile Val Thr Asp Gln Asn Asp Asn Lys Pro Lys
            20                  25                  30

Phe Thr Gln Asp Thr Phe Arg Gly Ser Val Leu
        35                  40
```

<210> SEQ ID NO 58
<211> LENGTH: 43
<212> TYPE: PRT
<213> ORGANISM: Homo sapien

<400> SEQUENCE: 58

```
Leu Phe Ser His Ala Val Ser Ser Asn Gly Asn Ala Val Glu Asp Pro
 1               5                  10                  15

Met Glu Ile Leu Ile Thr Val Thr Asp Gln Asn Asp Asn Lys Pro Glu
            20                  25                  30

Phe Thr Gln Glu Val Phe Lys Gly Ser Val Met
        35                  40
```

<210> SEQ ID NO 59
<211> LENGTH: 43
<212> TYPE: PRT
<213> ORGANISM: Gallus gallus

<400> SEQUENCE: 59

```
Leu Leu Ser His Ala Val Ser Ala Ser Gly Gln Pro Val Glu Asp Pro
 1               5                  10                  15

Met Glu Ile Ile Ile Thr Val Met Asp Gln Asn Asp Asn Lys Pro Val
            20                  25                  30

Phe Ile Lys Glu Val Phe Val Gly Tyr Ile Glu
        35                  40
```

<210> SEQ ID NO 60
<211> LENGTH: 43
<212> TYPE: PRT
<213> ORGANISM: Mus musculus

<400> SEQUENCE: 60

```
Leu Tyr Ser His Ala Val Ser Ser Asn Gly Glu Ala Val Glu Asp Pro
 1               5                  10                  15
```

-continued

```
Met Glu Ile Val Ile Thr Val Thr Asp Gln Asn Asp Asn Arg Pro Glu
            20                  25                  30

Phe Thr Gln Glu Val Phe Glu Gly Ser Val Ala
        35                  40


<210> SEQ ID NO 61
<211> LENGTH: 43
<212> TYPE: PRT
<213> ORGANISM: Xenopus laevis

<400> SEQUENCE: 61

Leu Phe Ser His Ala Val Ser Ser Asn Gly Ala Asn Val Glu Asp Pro
 1               5                  10                  15

Met Glu Ile Ile Ile Lys Val Gln Asp Gln Asn Asp Asn Asp Pro Val
            20                  25                  30

Phe Thr Gln Ser Val Phe Glu Gly Ser Val Pro
        35                  40


<210> SEQ ID NO 62
<211> LENGTH: 43
<212> TYPE: PRT
<213> ORGANISM: Xenopus laevis

<400> SEQUENCE: 62

Leu Leu Ser His Ala Val Ser Glu Asn Gly Ala Ser Val Glu Glu Pro
 1               5                  10                  15

Met Glu Ile Thr Val Thr Val Ile Asp Gln Asn Asp Asn Arg Pro Lys
            20                  25                  30

Phe Thr Gln Pro Val Phe Arg Gly Ser Val Arg
        35                  40


<210> SEQ ID NO 63
<211> LENGTH: 43
<212> TYPE: PRT
<213> ORGANISM: Xenopus laevis

<400> SEQUENCE: 63

Leu Ser Ser His Ala Val Ser Glu Asn Gly Ser Pro Val Glu Glu Pro
 1               5                  10                  15

Met Glu Ile Thr Ile Asn Val Ile Asp Gln Asn Asp Asn Arg Pro Lys
            20                  25                  30

Phe Thr Gln Asp Val Phe Arg Gly Ser Val Arg
        35                  40


<210> SEQ ID NO 64
<211> LENGTH: 43
<212> TYPE: PRT
<213> ORGANISM: Gallus gallus

<400> SEQUENCE: 64

Leu Tyr Ser His Ala Val Ser Glu Asn Gly Lys Pro Val Glu Glu Pro
 1               5                  10                  15

Met Glu Ile Ile Val Thr Val Thr Asp Gln Asn Asp Asn Lys Pro Gln
            20                  25                  30

Phe Thr Gln Glu Val Phe Arg Gly Ser Val Pro
        35                  40


<210> SEQ ID NO 65
<211> LENGTH: 43
<212> TYPE: PRT
```

-continued

<213> ORGANISM: Gallus gallus

<400> SEQUENCE: 65

Leu Arg Ala His Ala Val Asp Met Asn Gly Asn Lys Val Glu Asn Pro
1               5                   10                  15

Ile Asp Leu Tyr Ile Tyr Val Ile Asp Met Asn Asp Asn Arg Pro Glu
            20                  25                  30

Phe Ile Asn Gln Val Tyr Asn Gly Ser Val Asp
        35                  40

<210> SEQ ID NO 66
<211> LENGTH: 44
<212> TYPE: PRT
<213> ORGANISM: Drosophila melanogaster

<400> SEQUENCE: 66

Met Leu Lys His Ala Val Val Asn Leu Ile Asn Tyr Gln Asp Asp Ala
1               5                   10                  15

Glu Leu Ala Thr Arg Ala Ile Pro Glu Leu Ile Lys Leu Leu Asn Asp
            20                  25                  30

Glu Asp Gln Val Val Val Ser Gln Ala Ala Met Met
        35                  40

<210> SEQ ID NO 67
<211> LENGTH: 44
<212> TYPE: PRT
<213> ORGANISM: Homo sapien

<400> SEQUENCE: 67

Met Leu Lys His Ala Val Val Asn Leu Ile Asn Tyr Gln Asp Asp Ala
1               5                   10                  15

Glu Leu Ala Thr Arg Ala Ile Pro Glu Leu Thr Lys Leu Leu Asn Asp
            20                  25                  30

Glu Asp Gln Val Val Val Asn Lys Ala Ala Val Met
        35                  40

<210> SEQ ID NO 68
<211> LENGTH: 44
<212> TYPE: PRT
<213> ORGANISM: Xenopus laevis

<400> SEQUENCE: 68

Met Leu Lys His Ala Val Val Asn Leu Ile Asn Tyr Gln Asp Asp Ala
1               5                   10                  15

Glu Leu Ala Thr Arg Ala Ile Pro Glu Leu Thr Lys Leu Leu Asn Asp
            20                  25                  30

Glu Asp Gln Val Val Val Asn Lys Ala Ala Val Met
        35                  40

<210> SEQ ID NO 69
<211> LENGTH: 44
<212> TYPE: PRT
<213> ORGANISM: Urechis caupo

<400> SEQUENCE: 69

Met Leu Lys His Ala Val Val Asn Leu Ile Asn Tyr Gln Asp Asp Ala
1               5                   10                  15

Asp Leu Ala Thr Arg Ala Ile Pro Glu Leu Thr Lys Leu Leu Asn Asp
            20                  25                  30

Glu Asp Gln Val Val Val Ser Gln Ala Ala Met Met

-continued

```
        35                  40


<210> SEQ ID NO 70
<211> LENGTH: 44
<212> TYPE: PRT
<213> ORGANISM: Mus musculus

<400> SEQUENCE: 70

Met Leu Lys His Ala Val Val Asn Leu Ile Asn Tyr Gln Asp Asp Ala
 1               5                  10                  15

Glu Leu Ala Thr Arg Ala Ile Pro Glu Leu Thr Lys Leu Leu Asn Asp
            20                  25                  30

Glu Asp Gln Val Val Val Asn Lys Ala Ala Val Met
        35                  40


<210> SEQ ID NO 71
<211> LENGTH: 44
<212> TYPE: PRT
<213> ORGANISM: Lytechinus variegatus

<400> SEQUENCE: 71

Met Leu Lys His Ala Val Val Asn Leu Ile Asn Tyr Gln Asp Asp Ala
 1               5                  10                  15

Asp Leu Ala Thr Arg Ala Ile Pro Glu Leu Thr Lys Leu Leu Asn Asp
            20                  25                  30

Asp Asp Leu Val Val Val Asn Gln Ala Ala Val Met
        35                  40


<210> SEQ ID NO 72
<211> LENGTH: 22
<212> TYPE: PRT
<213> ORGANISM: Artificial Sequence
<220> FEATURE:
<223> OTHER INFORMATION: Modulating agent comprising beta-catenin HAV
      motif and a covalently linked Antennapedia internalization
      sequence

<400> SEQUENCE: 72

Lys His Ala Val Val Asn Arg Gln Ile Lys Ile Trp Pro Gln Asn Arg
 1               5                  10                  15

Arg Asn Lys Trp Lys Lys
            20


<210> SEQ ID NO 73
<211> LENGTH: 6
<212> TYPE: PRT
<213> ORGANISM: Artificial Sequence
<220> FEATURE:
<223> OTHER INFORMATION: Cyclic modulating agent

<400> SEQUENCE: 73

Cys Lys Ala Val Val Cys
 1               5


<210> SEQ ID NO 74
<211> LENGTH: 18
<212> TYPE: PRT
<213> ORGANISM: Artificial Sequence
<220> FEATURE:
<223> OTHER INFORMATION: Alpha-helix amphipathic model peptide

<400> SEQUENCE: 74

Lys Leu Ala Leu Lys Leu Ala Leu Lys Leu Ala Lys Ala Ala Leu Lys
 1               5                  10                  15
```

-continued

```
Leu Ala


<210> SEQ ID NO 75
<211> LENGTH: 11
<212> TYPE: PRT
<213> ORGANISM: Human immunodeficiency virus

<400> SEQUENCE: 75

Tyr Gly Arg Lys Lys Arg Arg Gln Arg Arg Arg
 1               5                  10
```

COMPOUNDS AND METHODS FOR STIMULATING GENE EXPRESSION AND CELLULAR DIFFERENTIATION

CROSS-REFERENCE TO RELATED APPLICATIONS

This application is a continuation-in-part of U.S. Ser. No. 09/057,363, filed Apr. 8, 1998, which claims the benefit of U.S. Provisional Application No. 60/043,361, filed on Apr. 10, 1997.

TECHNICAL FIELD

The present invention relates generally to compounds and methods for use in stimulating β-catenin mediated gene expression and cellular differentiation. The invention is more specifically related to modulating agents capable of increasing the level of free β-catenin in a cell cytoplasm, and to therapeutic methods employing such agents.

BACKGROUND OF THE INVENTION

β-catenin is a cytoplasmic protein that is critical for classical cadherin-mediated intercellular adhesion. Inside the cell, a β-catenin/α-catenin complex interacts with the second cytoplasmic domain (CP2) of the classical cadherins. In the absence of this β-catenin/α-catenin complex, the classical cadherins cannot promote cell adhesion (see Wheelock et al., *Current Topics in Membranes* 43:169–185, 1996).

β-Catenin is composed of 13 domains, referred to as arm repeats (FIG. 3). The arm repeat closest to the amino terminus of β-catenin (designated as the first arm repeat) is known to contain the α-catenin binding site. The specific amino acids that are directly involved in mediating the interaction between β-catenin and α-catenin have not previously been identified.

In addition to its role in cell adhesion, β-catenin also appears to be a key component of certain cellular signaling pathways, leading to activation of gene expression and a variety of developmental processes, such as differentiation. In particular, β-catenin functions in Wnt-mediated signaling, associating with LEF-1/TCF DNA binding proteins to form a transcription factor. The level of signal transduction appears to correlate with the level of free β-catenin in the cytoplasm of the cell (see Willert and Nusse, *Genetics and Development* 8:95–102, 1998).

Wnt-mediated signaling is involved in a variety of developmental processes, including cellular differentiation. For example, skin cells expressing a stabilized form of β-catenin display increased hair growth (Gat et al., *Cell* 95:605–614, 1998; Ono et al., *Cell* 95:575–578, 1998). Thus, therapies based on increasing the level of free β-catenin in the cytoplasm have potential for stimulating Wnt-mediated signal transduction, resulting in differentiation and, in certain instances, enhanced hair growth. However, there are presently no available therapies for modulating Wnt-mediated signaling.

Accordingly, there is a need in the art for improved methods for inducing Wnt-mediated signal transduction and cellular differentiation. The present invention fulfills this need and further provides other related advantages.

SUMMARY OF THE INVENTION

The present invention provides methods for stimulating β-catenin mediated gene transcription and cellular differentiation. Within certain aspects, the present invention provides modulating agents capable of increasing the level of free β-catenin in a cell. In one such aspect, the modulating agent comprises an internalization moiety and one or more of: (a) the amino acid sequence KHAVV (SEQ ID NO: 1); (b) a peptide analogue or peptidomimetic of the amino acid sequence KHAVV (SEQ ID NO: 1); or (c) an antibody or antigen-binding fragment thereof that specifically binds to a peptide comprising the amino acid sequence KHAVV (SEQ ID NO: 1). Within certain embodiments, the modulating agent comprises the sequence KHAVV (SEQ ID NO:1) within a linear peptide or a cyclic peptide ring. Such modulating agents may, within certain embodiments, comprise a linear or cyclic peptide ranging from 3 to 16 amino acid residues in length. The internalization moiety may comprise, within certain embodiments, an internalization sequence covalently linked to the modulating agent, a liposome that encapsulates the modulating agent or an antibody or ligand that binds to a cell surface receptor.

Within further embodiments, any of the above modulating agents may be linked to a targeting agent and/or a drug.

Within other aspects, the present invention provides pharmaceutical compositions comprising a modulating agent as described above, in combination with a pharmaceutically acceptable carrier.

The present invention further provides, within other aspects, methods for increasing the level of β-catenin in a cell, comprising contacting a cell with a modulating agent as described above.

Within further related aspects, the present invention provides methods for stimulating the activation of β-catenin mediated gene transcription in a cell, comprising contacting a cell with a modulating agent as described above.

Within further related aspects, the present invention provides methods for stimulating differentiation of a cell, comprising contacting a cell with a modulating agent as described above. In certain embodiments, the cell is a skin cell, such as a keratinocyte.

In other aspects, methods are provided for stimulating hair growth or reducing hair loss on a mammal, comprising administering to a mammal a modulating agent as described above. Such administration may be topical, and the skin cells may be present on the scalp of the mammal.

The present invention further provides, within other aspects, methods for stimulating exfoliation of skin on a mammal, comprising administering to a mammal a modulating agent as described above.

These and other aspects of the invention will become evident upon reference to the following detailed description and attached drawings. All references disclosed herein are hereby incorporated by reference in their entirety as if each were individually noted for incorporation.

BRIEF DESCRIPTION OF THE DRAWINGS

FIGS. 2A–2C provide the structures of representative cyclic peptides (SEQ ID NOs: 5, 23, 24, 26–34, 73) of the present invention.

FIG. 4 illustrates the local alignment of classical cadherins with β-catenins (SEQ ID NOs:52–71).

FIG. 7A shows untreated keratinocytes, and FIGS. 7B–7D show keratinocytes treated with 1 mg/ml KHAVVNRQIKIWPQNRRNKWKK (SEQ IN NO:72) for 48 hours. Squams are shown in FIGS. 7B and 7D by "Sq" and by arrows in FIG. 7C.

DETAILED DESCRIPTION OF THE INVENTION

Figure 3:
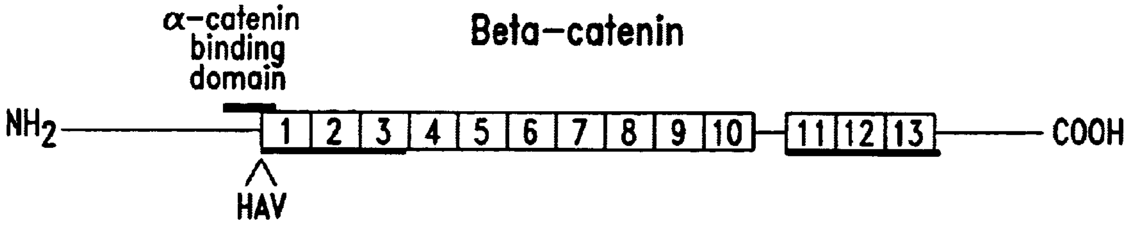
FIG. 3 is a diagram showing the structure of β-catenin.

As noted above, the present invention provides methods for stimulating β-catenin mediated gene transcription and cellular differentiation. The present invention is based, in part, upon the identification of an HAV motif within the first arm repeat of β-catenin (see FIG. 3) and the discovery that HAV-containing peptides are capable of disrupting interactions between α-catenin and β-catenin. The present invention is further based on the discovery that disrupting such interactions results in enhanced β-catenin mediated transcriptional activation, resulting in responses such as cellular differentiation. Without wishing to be bound by any particular theory, it is believed that this enhancement is the result of increased free β-catenin in the cytoplasm. Modulating agents that comprise HAV-containing peptides as provided herein may be used to stimulate β-catenin mediated gene transcription within a variety of contexts. For example, such agents may be used to stimulate hair growth or to stimulate exfoliation of skin.

Modulating Agents

As noted above, the term "modulating agent," as used herein, refers to a molecule comprising one or more of (1) a β-catenin HAV motif, (2) a peptide analogue or peptidomimetic thereof or (3) an antibody or antigen-binding fragment thereof that specifically binds to such a motif. A modulating agent is further capable of disrupting interactions between α-catenin and β-catenin, as described herein. Within preferred embodiments, a modulating agent further comprises an internalization moiety, which is associated (covalently or noncovalently) with one or more of the above components.

As used herein, a "β-catenin HAV motif" comprises the tripeptide sequence HAV. Within certain preferred embodiments, the β-catenin HAV motif further comprises at least one, and more preferably at least two or three, amino acid residues that flank the HAV sequence in a native β-catenin molecule (i.e., residues that are adjacent to the HAV sequence located within the first arm repeat of a native β-catenin molecule). Flanking sequences for β-catenin of a variety of organisms are shown in SEQ ID NOs:52 to 71, and FIG. 4. Flanking sequences are preferably derived from the sequence LKHAVVNLIN (SEQ ID NO:7). Flanking residue(s) may be present on the N-terminal and/or C-terminal side of an HAV motif, preferably on both sides. Within certain preferred embodiments, a modulating agent comprises the β-catenin HAV motif KHAVV (SEQ ID NO: 1). A modulating agent may consist entirely of a β-catenin HAV motif, or may additionally comprise further peptide and/or non-peptide regions, such as regions that facilitate cyclization, purification or other manipulation, and/or residues having a targeting or other function. Modulating agents may further be associated (covalently or noncovalently) with a targeting agent, drug, solid support and/or detectable marker.

Modulating agents, or peptide portions thereof, may be linear or cyclic peptides. A "linear" peptide is a peptide or salt thereof that does not contain an intramolecular covalent bond between two non-adjacent residues. Within preferred embodiments, linear peptide modulating agents typically comprise from 5 to about 20 amino acid residues, preferably from 5 to 16 amino acid residues and more preferably from 5 to 10 amino acid residues. Linear peptides that may be present within a modulating agent include, but are not limited to, KHAVVN (SEQ ID NO:8), LKHAVVN (SEQ ID NO:9), LKHAVV (SEQ ID NO:10), LKHAV (SEQ ID NO:11), KHAVV (SEQ ID NO:1), CKHAVVNC (SEQ ID NO:4), CLKHAVVNC (SEQ ID NO:12), CLKHAVVC (SEQ ID NO:13), CLKHAVC (SEQ ID NO:14), CKHAVVC (SEQ ID NO:15), KHAV (SEQ ID NO:16), HAVVN (SEQ ID NO:17), HAVN (SEQ ID NO:18), HAV, CKHAVC (SEQ ID NO:19), CHAVVNC (SEQ ID NO:20), CHAVVC (SEQ ID NO:21) and CHAVC (SEQ ID NO:22), as well as derivatives of the foregoing sequences having one or more side chain modifications.

The term "cyclic peptide," as used herein, refers to a peptide or salt thereof that comprises an intramolecular covalent bond between two non-adjacent residues, forming a cyclic peptide ring that comprises the β-catenin HAV motif, or analogue thereof. The intramolecular bond may be a backbone to backbone, side-chain to backbone or side-chain to side-chain bond (ie., terminal functional groups of a linear peptide and/or side chain functional groups of a terminal or interior residue may be linked to achieve cyclization). Preferred intramolecular bonds include, but are not limited to, disulfide bonds; amide bonds between terminal functional groups, between residue side chains or between one terminal functional groups and one residue side chain; thioether bonds and $\delta_1,\delta_{1'}$-ditryptophan or a derivative thereof. Preferred cyclic peptide modulating agents generally comprise from 4 to 15 residues, more preferably from 5 to 10 residues, within the cyclic peptide ring. Preferred cyclic peptides include CKHAVVNC (SEQ ID NO:5), CLKHAVVNC (SEQ ID NO:23), CLKHAVVC (SEQ ID NO:24), CKHAVVC (SEQ ID NO:25), KHAVVND (SEQ ID NO:26), KHAVVNE (SEQ ID NO:27), KHAVVD (SEQ ID NO:28), KHAVVE (SEQ ID NO:29), CLKHAVC (SEQ ID NO:30), CKHAVC (SEQ ID NO:31), CHAVVNC (SEQ ID NO:32), CHAVVC (SEQ ID NO:33), CHAVC (SEQ ID NO:34), KHAVD (SEQ ID NO:35) and KHAVE (SEQ ID NO:36), where the underline indicates cyclization, as well as derivatives of the foregoing sequences having one or more side chain modifications.

As noted above, modulating agents may be polypeptides or salts thereof, containing only amino acid residues linked by peptide bonds, or may additionally contain non-peptide regions, such as linkers. Peptide regions of a modulating agent may comprise residues of L-amino acids, D-amino acids, or any combination thereof. Amino acids may be from natural or non-natural sources, provided that at least one amino group and at least one carboxyl group are present in the molecule; α- and β-amino acids are generally preferred.

The 20 L-amino acids commonly found in proteins are identified herein by the conventional three-letter or one-letter abbreviations shown in Table 1.

TABLE 1

| Amino acid one-letter and three-letter abbreviations | | |
|---|---|---|
| A | Ala | Alanine |
| R | Arg | Arginine |
| D | Asp | Aspartic acid |
| N | Asn | Asparagine |
| C | Cys | Cysteine |
| Q | Gln | Glutamine |
| E | Glu | Glutamic acid |
| G | Gly | Glycine |
| H | His | Histidine |
| I | Ile | Isoleucine |
| L | Leu | Leucine |
| K | Lys | Lysine |
| M | Met | Methionine |
| F | Phe | Phenylalanine |
| P | Pro | Proline |
| S | Ser | Serine |
| T | Thr | Threonine |
| W | Trp | Tryptophan |
| Y | Tyr | Tyrosine |
| V | Val | Valine |

A modulating agent may also contain rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Preferred derivatives include amino acids having a C-terminal amide group. Residues other than common amino acids that may be present with a modulating agent include, but are not limited to, 2-mercaptoaniline, 2-mercaptoproline, ornithine, diaminobutyric acid, α-aminoadipic acid, m-aminomethylbenzoic acid and α,β-diaminopropionic acid.

As noted above, a modulating agent may comprise a peptide analogue or a non-peptide peptidomimetic of a native β-catenin HAV motif, provided that the analogue or peptidomimetic retains the ability to disrupt an interaction between α-catenin and β-catenin. In general, a peptide analogue of a native β-catenin sequence should retain the HAV sequence, but may contain conservative substitutions at one or more flanking residues such that the ability to disrupt interactions between α-catenin and β-catenin is not diminished. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. The critical determining feature of a peptide analogue is the ability to disrupt an interaction between α- and β-catenin. Such an ability may be evaluated using the representative assays provided herein.

A peptidomimetic is a non-peptide compound that is structurally similar to a β-catenin HAV motif, such that it retains the ability to disrupt interactions between α-catenin and β-catenin, as described below. Peptidomimetics are organic compounds that mimic the three-dimensional shape of a β-catenin HAV motif. Peptidomimetics may be designed based on techniques that evaluate the three dimensional shape, such as nuclear magnetic resonance (NMR) and computational techniques. NMR is widely used for structural analysis of molecules. Cross-peak intensities in nuclear Overhauser enhancement (NOE) spectra, coupling constants and chemical shifts depend on the conformation of a compound. NOE data provide the interproton distance between protons through space. This information may be used to facilitate calculation of the lowest energy conformation for the HAV motif. Once the lowest energy conformation is known, the three-dimensional shape to be mimicked is known. It should be understood that, within embodiments described herein, an analogue or peptidomimetic may be substituted for a native HAV motif.

Peptide modulating agents (and peptide portions of modulating agents) as described herein may be synthesized by methods well known in the art, including chemical synthesis and recombinant DNA methods. For modulating agents up to about 50 residues in length, chemical synthesis may be performed using solution phase or solid phase peptide synthesis techniques, in which a peptide linkage occurs through the direct condensation of the α-amino group of one amino acid with the α-carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (see Gross and Meienhofer, eds., "The Peptides: Analysis, Synthesis, Biology," Vol. 1–4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solution synthesis requires consideration of main chain and side chain protecting groups and activation method. In addition, careful segment selection is necessary to minimize racemization during segment condensation. Solubility considerations are also a factor.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., *J. Am. Chem. Soc.* 85:2149, 1963, which involves assembling a linear peptide chain on a resin support using protected amino acids. Solid phase peptide synthesis typically utilizes either the Boc or Fmoc strategy. The Boc strategy uses a 1% cross-linked polystyrene resin. The standard protecting group for α-amino functions is the tert-butyloxycarbonyl (Boc) group. This group can be removed with dilute solutions of strong acids such as 25% trifluoroacetic acid (TFA).

The next Boc-amino acid is typically coupled to the amino acyl resin using dicyclohexylcarbodiimide (DCC). Following completion of the assembly, the peptide-resin is treated with anhydrous HF to cleave the benzyl ester link and liberate the free peptide. Side-chain functional groups are usually blocked during synthesis by benzyl-derived blocking groups, which are also cleaved by HF. The free peptide is then extracted from the resin with a suitable solvent, purified and characterized. Newly synthesized peptides can be purified, for example, by gel filtration, HPLC, partition chromatography and/or ion-exchange chromatography, and may be characterized by, for example, mass spectrometry or amino acid sequence analysis. In the Boc strategy, C-terminal amidated peptides can be obtained using benzhydrylamine or methylbenzhydrylamine resins, which yield peptide amides directly upon cleavage with HF.

In the procedures discussed above, the selectivity of the side-chain blocking groups and of the peptide-resin link depends upon the differences in the rate of acidolytic cleavage. Orthoganol systems have been introduced in which the side-chain blocking groups and the peptide-resin link are completely stable to the reagent used to remove the α-protecting group at each step of the synthesis. The most common of these methods involves the 9-fluorenylmethyloxycarbonyl (Fmoc) approach. Within this method, the side-chain protecting groups and the peptide-resin link are completely stable to the secondary amines used for cleaving the N-α-Fmoc group. The side-chain protection and the peptide-resin link are cleaved by mild acidolysis. The repeated contact with base makes the Merrifield resin unsuitable for Fmoc chemistry, and p-alkoxybenzyl esters linked to the resin are generally used. Deprotection and cleavage are generally accomplished using TFA.

Those of ordinary skill in the art will recognize that, in solid phase synthesis, deprotection and coupling reactions must go to completion and the side-chain blocking groups must be stable throughout the entire synthesis. In addition, solid phase synthesis is generally most suitable when peptides are to be made on a small scale.

Acetylation of the N-terminus can be accomplished by reacting the final peptide with acetic anhydride before cleavage from the resin. C-amidation may be accomplished using an appropriate resin such as methylbenzhydrylamine resin using the Boc technology.

Following synthesis of a linear peptide, cyclization may be achieved if desired by any of a variety of techniques well known in the art. Within one embodiment, a bond may be generated between reactive amino acid side chains. For example, a disulfide bridge may be formed from a linear peptide comprising two thiol-containing residues by oxidizing the peptide using any of a variety of methods. Within one such method, air oxidation of thiols can generate disulfide linkages over a period of several days using either basic or neutral aqueous media. The peptide is used in high dilution to minimize aggregation and intermolecular side reactions. This method suffers from the disadvantage of being slow but has the advantage of only producing $H_2O$ as a side product. Alternatively, strong oxidizing agents such as $I_2$ and $K_3Fe(CN)_6$ can be used to form disulfide linkages. Those of ordinary skill in the art will recognize that care must be taken not to oxidize the sensitive side chains of Met, Tyr, Trp or His. Cyclic peptides produced by this method require purification using standard techniques, but this oxidation is applicable at acid pHs. Oxidizing agents also allow concurrent deprotection/oxidation of suitable S-protected linear precursors to avoid premature, nonspecific oxidation of free cysteine.

DMSO, unlike $I_2$ and $K_3Fe(CN)_6$, is a mild oxidizing agent which does not cause oxidative side reactions of the nucleophilic amino acids mentioned above. DMSO is miscible with $H_2O$ at all concentrations, and oxidations can be performed at acidic to neutral pHs with harmless byproducts. Methyltrichlorosilane-diphenylsulfoxide may alternatively be used as an oxidizing agent, for concurrent deprotection/oxidation of S-Acm, S-Tacm or S-t-Bu of cysteine without affecting other nucleophilic amino acids. There are no polymeric products resulting from intermolecular disulfide bond formation. Suitable thiol-containing residues for use in such oxidation methods include, but are not limited to, cysteine, β,β-dimethyl cysteine (penicillamine or Pen), β,β-tetramethylene cysteine (Tmc), β,β-pentamethylene cysteine (Pmc), β-mercaptopropionic acid (Mpr), β,β-pentamethylene-β-mercaptopropionic acid (Pmp), 2-mercaptobenzene, 2-mercaptoaniline and 2-mercaptoproline. Peptides containing such residues are illustrated by the following representative formulas, in which the underlined portion is cyclized, N-acetyl groups are indicated by N-Ac and C-terminal amide groups are represented by $—NH_2$:

i) H-<u>Lys-His-Ala-Val-Val-Asn</u>-OH (SEQ ID NO:37)

ii) H-<u>Leu-Lys-His-Ala-Val-Val-Asn</u>-OH (SEQ ID NO:38)

iii) H-<u>His-Ala-Val-Val-Asn</u>-OH (SEQ ID NO:39)

iv) H-<u>His-Ala-Val-Val</u>-OH (SEQ ID NO:40)

v) H-<u>Cys-Lys-His-Ala-Val-Val-Asn-Cys</u>-OH (SEQ ID NO:5)

vi) H-<u>Cys-Leu-Lys-His-Ala-Val-Val-Asn-Cys</u>-OH (SEQ ID NO:23)

vii) H-<u>Cys-His-Ala-Val-Val-Asn-Cys</u>-OH (SEQ ID NO:32)

viii) H-<u>Cys-His-Ala-Val-Val-Cys</u>-OH (SEQ ID NO:33)

ix) H-<u>Cys-Lys-His-Ala-Val-Val-Asn-Pen</u>-OH (SEQ ID NO:41)

x) H-<u>Tmc-Lys-His-Ala-Val-Val-Asn-Cys</u>-OH (SEQ ID NO:42)

xi) H-<u>Pmc-Lys-His-Ala-Val-Val-Asn-Cys</u>-OH (SEQ ID NO:43)

xii) H-<u>Mpr-Lys-His-Ala-Val-Val-Asn-Cys</u>-OH (SEQ ID NO:44)

xiii) H-<u>Pmp-Lys-His-Ala-Val-Val-Asn-Cys</u>-OH (SEQ ID NO:45)

It will be readily apparent to those of ordinary skill in the art that, within each of these representative formulas, any of the above thiol-containing residues may be employed in place of one or both of the thiol-containing residues recited.

Within another embodiment, cyclization may be achieved by amide bond formation. For example, a peptide bond may be formed between terminal functional groups (i.e., the amino and carboxy termini of a linear peptide prior to cyclization), with or without an N-terminal acetyl group and/or a C-terminal amide. Within another such embodiment, the linear peptide comprises a D-amino acid. Alternatively, cyclization may be accomplished by linking one terminus and a residue side chain or using two side chains, with or without an N-terminal acetyl group and/or a C-terminal amide. Residues capable of forming a lactam bond include lysine, ornithine (Orn), α-amino adipic acid, m-aminomethylbenzoic acid, α,β-diaminopropionic acid, glutamate or aspartate.

Methods for forming amide bonds are well known in the art and are based on well established principles of chemical reactivity. Within one such method, carbodiimide-mediated lactam formation can be accomplished by reaction of the carboxylic acid with DCC, DIC, EDAC or DCCI, resulting in the formation of an O-acylurea that can be reacted immediately with the free amino group to complete the cyclization. The formation of the inactive N-acylurea, resulting from O→N migration, can be circumvented by converting the O-acylurea to an active ester by reaction with an N-hydroxy compound such as 1-hydroxybenzotriazole, 1-hydroxysuccinimide, 1-hydroxynorbornene carboxamide or ethyl 2-hydroximino-2-cyanoacetate. In addition to minimizing O→N migration, these additives also serve as catalysts during cyclization and assist in lowering racemization. Alternatively, cyclization can be performed using the azide method, in which a reactive azide intermediate is generated from an alkyl ester via a hydrazide. Hydrazinolysis of the terminal ester necessitates the use of a t-butyl group for the protection of side chain carboxyl functions in the acylating component. This limitation can be overcome by using diphenylphosphoryl acid (DPPA), which furnishes an azide directly upon reaction with a carboxyl group. The slow reactivity of azides and the formation of isocyanates by their disproportionation restrict the usefulness of this method. The mixed anhydride method of lactam formation is widely used because of the facile removal of reaction by-products. The anhydride is formed upon reaction of the carboxylate anion with an alkyl chloroformate or pivaloyl chloride. The attack of the amino component is then guided to the carbonyl carbon of the acylating component by the electron donating effect of the alkoxy group or by the steric bulk of the pivaloyl chloride t-butyl group, which obstructs attack on the wrong carbonyl group. Mixed anhydrides with phosphoric acid derivatives have also been successfully used. Alternatively, cyclization can be accomplished using activated esters. The presence of electron withdrawing substituents on the alkoxy carbon of esters increases their susceptibility to aminolysis. The high reactivity of esters of p-nitrophenol, N-hydroxy compounds and polyhalogenated phenols has made these "active esters" useful in the synthesis of amide bonds. The last few years have witnessed the development of benzotriazolyloxytris-(dimethylamino) phosphonium hexafluorophosphonate (BOP) and its congeners as advantageous coupling reagents. Their performance is generally superior to that of the well established carbodiimide amide bond formation reactions.

Within a further embodiment, a thioether linkage may be formed between the side chain of a thiol-containing residue and an appropriately derivatized α-amino acid. By way of example, a lysine side chain can be coupled to bromoacetic acid through the carbodiimide coupling method (DCC, EDAC) and then reacted with the side chain of any of the thiol containing residues mentioned above to form a thioether linkage. In order to form dithioethers, any two thiol containing side-chains can be reacted with dibromoethane and diisopropylamine in DMF. Examples of thiol-containing linkages are shown below:

i.

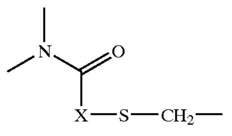

$X = (CH_2)_4$
$= CH_2$

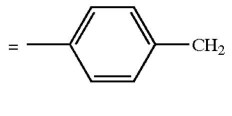

-continued ii.

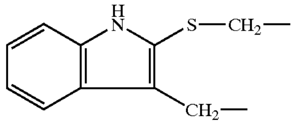

Cyclization may also be achieved using $\delta_1,\delta_1$-Ditryptophan (i.e., Ac-Trp-Gly-Gly-Trp-OMe) (SEQ ID NO:46), as shown below:

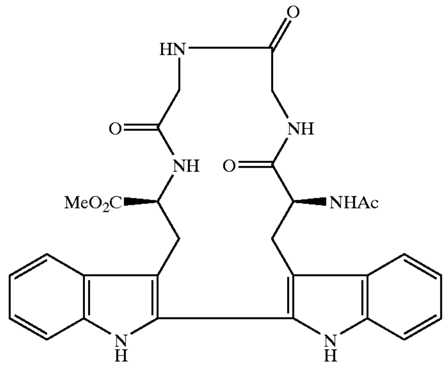

Figure 1:
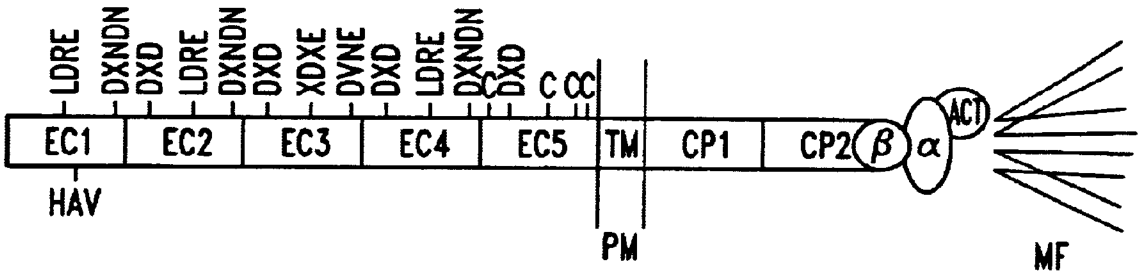
FIG. 1 is a schematic diagram showing the structure of a classical cadherin and its interaction with the catenins. The five extracellular domains are designated EC1–EC5, the hydrophobic domain that transverses the plasma membrane (PM) is represented by TM, and the two cytoplasmic domains are represented by CP1 and CP2. The calcium binding motifs are shown by DXNDN (SEQ ID NO:2), DXD and LDRE (SEQ ID NO:3). The CAR sequence, HAV, is shown within EC1. Cytoplasmic proteins β-catenin (β), α-catenin (α) and α-actinin (ACT), as well as microfilaments (MF), are also shown.
Figure 2C:
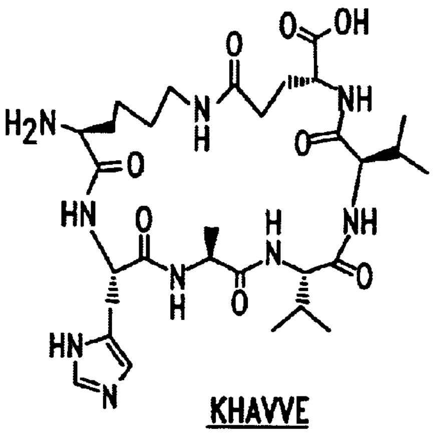

Representative cyclic peptide modulating agents are depicted in FIG. 2. The structures and formulas recited herein are provided solely for the purpose of illustration, and are not intended to limit the scope of the modulating agents described herein.

For longer peptide modulating agents, recombinant methods are preferred for synthesis. Within such methods, all or part of a modulating agent can be synthesized in living cells, using any of a variety of expression vectors known to those of ordinary skill in the art to be appropriate for the particular host cell. Suitable host cells may include bacteria, yeast cells, mammalian cells, insect cells, plant cells, algae and other animal cells (e.g., hybridoma, CHO, myeloma). The DNA sequences expressed in this manner may encode portions of an endogenous β-catenin and/or other sequences. Endogenous β-catenin sequences may be prepared based on known cDNA or genomic sequences (see Wheelock et al., *Current Topics in Membranes* 43:169–185, 1996), which may be isolated by screening an appropriate library with probes designed based on such known sequences. Screens may generally be performed as described in Sambrook et al., *Molecular Cloning. A Laboratory Manual*, Cold Spring Harbor Laboratories, Cold Spring Harbor, N.Y., 1989 (and references cited therein). Polymerase chain reaction (PCR) may also be employed, using oligonucleotide primers in methods well known in the art, to isolate nucleic acid molecules encoding all or a portion of an endogenous β-catenin. To generate a nucleic acid molecule encoding a desired modulating agent, an endogenous β-catenin sequence may be modified using well known techniques. For example, portions encoding one or more HAV motifs may be joined, with or without separation by unrelated nucleic acid regions. Alternatively, portions of the desired nucleic acid sequences may be synthesized using well known techniques, and then ligated together to form a sequence encoding the modulating agent.

As noted above, a modulating agent may comprise an antibody, or antigen-binding fragment thereof, that specifically binds to a β-catenin HAV motif. As used herein, an antibody, or antigen-binding fragment thereof, is said to "specifically bind" to such a motif if it reacts at a detectable level (within, for example, an ELISA) with a peptide containing the motif, and does not react detectably with peptides that do not contain a β-catenin HAV motif.

Antibodies and fragments thereof may be prepared using standard techniques. See, e.g., Harlow and Lane, *Antibodies: A Laboratory Manual*, Cold Spring Harbor Laboratory, 1988. In one such technique, an immunogen comprising a β-catenin HAV motif is initially injected into any of a wide variety of mammals (e.g., mice, rats, rabbits, sheep or goats). Small immunogens (i.e., less than about 20 amino acids) should be joined to a carrier protein, such as bovine serum albumin or keyhole limpet hemocyanin. Following one or more injections, the animals are bled periodically. Polyclonal antibodies specific for the β-catenin HAV motif may then be purified from such antisera by, for example, affinity chromatography using the modulating agent or antigenic portion thereof coupled to a suitable solid support.

Monoclonal antibodies specific for a β-catenin HAV motif may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity from spleen cells obtained from an animal immunized as described above. The spleen cells are immortalized by, for example, fusion with a myeloma cell fusion partner, preferably one that is syngeneic with the immunized animal. Single colonies are selected and their culture supernatants tested for binding activity against the modulating agent or antigenic portion thereof. Hybridomas having high reactivity and specificity are preferred. To evaluate the specificity of a particular antibody, conventional antigen-binding assays may be employed.

Monoclonal antibodies may be isolated from the supernatants of growing hybridoma colonies, with or without the use of various techniques known in the art to enhance the yield. Contaminants may be removed from the antibodies by conventional techniques, such as chromatography, gel filtration, precipitation, and extraction. Antibodies having the desired activity may generally be identified using immunofluorescence analyses of tissue sections, cell or other samples where the target catenin is localized.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988; see especially page 309) and digested by papain to yield Fab and Fc fragments. The Fab and Fc fragments may be separated by affinity chromatography on protein A bead columns (Harlow and Lane, 1988, pages 628–29).

Within certain embodiments, it may be beneficial to employ modulating agents that comprise an associated internalization moiety. An internalization moiety is any moiety (such as a compound, liposome or particle) that can be used to improve the ability of an agent to penetrate the lipid bilayer of the cellular plasma membrane, thus enabling the agent to readily enter the cytoplasm and disrupt interactions between intracellular α-catenin and β-catenin. As used herein, the term "associated with" refers to covalent attachment or a non-covalent interaction mediated by, for example, ionic bonds, hydrogen bonds, van der waals forces and/or hydrophobic interactions, such that the internalization moiety and modulating agent remain in close proximity under physiological conditions.

Within certain embodiments, an internalization moiety is an internalization sequence. An internalization sequence may be any sequence (generally a peptide sequence) that is capable of facilitating entry of the modulating agent into the cytosol of a living cell. One suitable internalization sequence is a 16 amino acid peptide derived from the third helix of the Antennapedia protein, and having the sequence RQIKIWFQNRRMKWKK (SEQ ID NO:47; see Prochiantz, *Curr. Op. Neurobiol.* 6:629–34, 1996) or RQIKIWPQNRRNKWKK (SEQ ID NO:48). Analogues of this sequence (i.e., sequences having at least 25% sequence identity, such that the ability to facilitate entry into the cytosol is not diminished) may also be employed. One such analogue is KKWKKWWKKWWKKWKK (SEQ ID NO:49). One preferred modulating agent that comprises a covalently linked Antennapedia internalization sequence has the sequence KHAVVNRQIKIWFQNRRMKWKK (SEQ ID NO:50).

Alternatively, an internalization sequence may be unrelated to the Antennapedia sequence. Any sequence that facilitates entry to the cell, via a cell surface receptor or other means, may be employed. Protein-derived helical peptide sequences that may be used as internalization sequences include, but are not limited to, KLALKLALKLAKAALKLA (SEQ ID NO:74; see Oehlke et al., *Biochim. Biophys. Acta* 1414:127–139, 1998, and references cited therein). Other internalization sequences include the 11 amino acid TAT protein transduction domain YGRKKRRQRRR (SEQ ID NO:75; see Nagahara et al., *Nature Medicine* 4:1449–1452, 1998) and the transduction domain of HSV VP22 (see Elliot and O'Hare, *Cell* 88:223–244, 1997).

In general, the ability of a sequence to facilitate entry into the cytosol may be evaluated by covalently linking such a sequence to a known modulating agent and evaluating the ability of the modulating agent to disrupt interactions between α-catenin and β-catenin, as described herein. Within such an assay, an internalization sequence should permit a level of disruption that is statistically greater than that observed in the absence of internalization sequence. Preferably, an internalization sequence incorporated into a modulating agent results in a level of disruption that is comparable to, or greater than, that observed for the modulating agent comprising an internalization sequence derived from Antennapedia.

An internalization sequence may be covalently linked to a modulating agent. Such linkage may be generated using any of a variety of means well known in the art, either directly or by way of a spacer. In general, spacers may be amino acid residues (e.g., amino hexanoic acid) or peptides, or may be other bi- or multi-functional compounds that can be covalently linked to at least two peptide sequences. Covalent linkage may be achieved via direct condensation or other well known techniques.

Other internalization moieties may also be employed. In general, any moiety that permits a level of disruption that is statistically greater than that observed in its absence is considered an internalization moiety. Preferably, an internalization moiety results in a level of disruption that is comparable to, or greater than, that observed for the modulating agent associated with an internalization sequence derived from Antennapedia, as described above. For example, a modulating agent may be incorporated into a liposome (i.e., an artificial membrane vesicle), using well known technology. Other internalization moieties include, but are not limited to, antibodies and ligands that bind to cell surface receptors. Alternatively, a polynucleotide encoding a modulating agent may be incorporated into an appropriate viral vector, such that the modulating agent is generated within the target cell. Various particle-mediated delivery systems are also available, and their use is well known to those of ordinary skill in the art.

Evaluation of Modulating Agent Activity

As noted above, modulating agents are capable of disrupting an interaction between α-catenin and β-catenin. This ability may generally be evaluated using any suitable assay known to those of ordinary skill in the art. For example, an immunoprecipitation assay as described herein may be employed. Within such an assay, disruption of the interaction is measured by assessing the ability of an antibody directed against β-catenin to immunoprecipitate α-catenin in the presence and absence of the modulating agent. For example, tissue such as brain may be homogenized in the presence and absence of modulating agent. The ability of an antibody directed against β-catenin to immunoprecipitate α-catenin from the homogenate is then assessed by probing a Western blot of proteins immunoprecipitated from the tissue homogenate by anti-β-catenin antibody with an anti-α-catenin antibody. The resulting signal is indicative of the level of interaction between α-catenin and β-catenin. In general, a modulating agent should inhibit such interaction by at least 50%.

The effect of a modulating agent on β-catenin mediated gene transcription may be determined using any appropriate assay, such as the keratinocyte differentiation assay provided herein. Briefly, keratinocytes may be treated with a candidate modulating agent (e.g., 1 mg/ml for 48 hours). Treated and untreated cells are then photographed. At a concentration of 1 mg/ml, a modulating agent should detectably induce the formation of terminally differentiated cells known as squams, which may be identified based on detachment from the substratum, and morphological alterations that are well known to those of ordinary skill in the art.

Other suitable assays are those designed to detect changes in hair growth. Such assays may be performed using plucked hair or hair follicles cultured in vitro. Such assays are described, for example, within U.S. Pat. Nos. 5,527,772 and 5,739,111. For assays using hair, the effect of a modulating agent may be determined based on DNA content in the hair. Increased DNA content should be observed in hair cultured for 48 hours in the presence of 1 mg/ml modulating agent, relative to hair cultured in the absence of modulating agent. In vivo assays may be performed, for example, by application of a modulating agent to shaved skin on a mouse, in which a modulating agent results in increased hair density and/or hair length.

Modulating agents also inhibit cadherin-mediated cell adhesion, and assays to evaluate this property may be used instead of, or in addition to, an immunoprecipitation assay or keratinocyte differentiation assay. This property may be evaluatcd using any of a variety of in vitro assays designed to measure the effect of the peptide on a typical cadherin response. The ability of an agent to modulate cell adhesion may generally be evaluated in vitro by assaying the effect on one or more of the following: (1) adhesion between endothelial cells, (2) adhesion between epithelial cells (e.g., normal rat kidney cells and/or human skin) and/or (3) adhesion between cancer cells. In general, a modulating agent is an inhibitor of cell adhesion if, within one or more of these representative assays, contact of the test cells with the modulating agent results in a discernible disruption of cell adhesion.

In general, the addition of a modulating agent to cells that express a cadherin results in disruption of cell adhesion. A "cadherin-expressing cell," as used herein, may be any type of cell that expresses at least one cadherin on the cell surface at a detectable level, using standard techniques such as immunocytochemical protocols (e.g., Blaschuk and Farookhi, *Dev. Biol.* 136:564–567, 1989). Cadherin-expressing cells include endothelial, epithelial and/or cancer cells. For example, such cells may be plated under standard conditions that, in the absence of modulating agent, permit cell adhesion. In the presence of modulating agent (e.g., 500 μg/mL), disruption of cell. adhesion may be determined visually within 24 hours, by observing retraction of the cells from one another.

For use within one such assay, bovine pulmonary artery endothelial cells may be harvested by sterile ablation and digestion in 0.1% collagenase (type II; Worthington Enzymes, Freehold, N.J.). Cells may be maintained in Dulbecco's minimum essential medium supplemented with 10% fetal calf serum and 1% antibiotic-antimycotic at 37° C. in 7% $CO_2$ in air. Cultures may be passaged weekly in trypsin-EDTA and seeded onto tissue culture plastic at 20,000 cells/$cm^2$. Endothelial cultures may be used at 1 week in culture, which is approximately 3 days after culture confluency is established. The cells may be seeded onto coverslips and treated (e.g., for 30 minutes) with modulating agent or a control compound at, for example, 500 μg/ml and then fixed with 1% paraformaldehyde. As noted above, disruption of cell adhesion may be determined visually within 24 hours, by observing retraction of the cells from one another. This assay evaluates the effect of a modulating agent on N-cadherin mediated cell adhesion.

Within another such assay, the effect of a modulating agent on normal rat kidney (NRK) cells may be evaluated. According to a representative procedure, NRK cells (ATCC #1571-CRL) may be plated at 10–20,000 cells per 35 mm tissue culture flasks containing DMEM with 10% FCS and sub-cultured periodically (Laird et al., *J Cell Biol.* 131:1193–1203, 1995). Cells may be harvested and replated in 35 mm tissue culture flasks containing 1 mm coverslips and incubated until 50–65% confluent (24–36 hours). At this time, coverslips may be transferred to a 24-well plate, washed once with fresh DMEM and exposed to modulating agent at a concentration of, for example, 1 mg/mL for 24 hours. Fresh modulating agent may then be added, and the cells left for an additional 24 hours. Cells may be fixed with 100% methanol for 10 minutes and then washed three times with PBS. Coverslips may be blocked for 1 hour in 2% BSA/PBS and incubated for a further 1 hour in the presence of mouse anti-E-cadherin antibody (Transduction Labs, 1:250 dilution). Primary and secondary antibodies may be diluted in 2% BSA/PBS. Following incubation in the primary antibody, coverslips may be washed three times for 5 minutes each in PBS and incubated for 1 hour with donkey anti-mouse antibody conjugated to fluorescein (diluted 1:200). Following further washes in PBS (3×5 min) coverslips can be mounted and viewed by confocal microscopy.

In the absence of modulating agent, NRK cells form characteristic tightly adherent monolayers with a cobblestone morphology in which cells display a polygonal shape. NRK cells that are treated with a modulating agent that disrupts E-cadherin mediated cell adhesion may assume a non-polygonal and elongated morphology (i.e., a fibroblast-like shape) within 48 hours of treatment with 1 mg/mL of modulating agent. Gaps appear in confluent cultures of such cells. In addition, 1 mg/mL of such a modulating agent reproducibly induces a readily apparent reduction in cell surface staining of E-cadherin, as judged by immunofluorescence microscopy (Laird et al., *J. Cell Biol.* 131:1193–1203, 1995), of at least 75% within 48 hours.

A third cell adhesion assay involves evaluating the effect of a modulating agent on permeability of adherent epithelial and/or endothelial cell layers. For example, the effect of permeability on human skin may be evaluated. Such skin may be derived from a natural source or may be synthetic. Human abdominal skin for use in such assays may generally be obtained from humans at autopsy within 24 hours of death. Briefly, a modulating agent (e.g., 500 μg/ml) and a test marker (e g., the fluorescent markers Oregon Green™ and Rhodamine Green™ Dextran) may be dissolved in a sterile buffer (e.g., phosphate buffer, pH 7.2), and the ability of the marker to penetrate through the skin and into a receptor fluid (e.g., phosphate buffer) may be measured using a Franz Cell apparatus (Franz, *Curr. Prob. Dermatol.* 7:58–68, 1978; Franz, *J. Invest. Dermatol.* 64:190–195, 1975). The penetration of the markers through the skin may be assessed at, for example, 6, 12, 24, 36, and 48 hours after the start of the experiment. In general, a modulating agent results in a statistically significant increase in the amount of marker in the receptor compartment after 6–48 hours in the presence of 500 μg/mL modulating agent. This assay evaluates the effect of a modulating agent on E-cadherin mediated cell adhesion.

Modulating Agent Modification and Formulations

A modulating agent as described herein may, but need not, be linked to one or more additional molecules. Although modulating agents as described herein may preferentially bind to specific tissues or cells, and thus may be sufficient to target a desired site in vivo, it may be beneficial for certain applications to include an additional targeting agent. Accordingly, a targeting agent may be associated with a modulating agent to facilitate targeting to one or more specific tissues. As used herein, a "targeting agent" may be any substance (such as a compound or cell) that, when associated with a modulating agent enhances the transport of the modulating agent to a target tissue, thereby increasing the local concentration of the modulating agent. Targeting agents include antibodies or fragments thereof, receptors, ligands and other molecules that bind to cells of, or in the vicinity of, the target tissue. Known targeting agents include serum hormones, antibodies against cell surface antigens, lectins, adhesion molecules, tumor cell surface binding ligands, steroids, cholesterol, lymphokines, fibrinolytic enzymes and those drugs and proteins that bind to a desired target site. Among the many monoclonal antibodies that may serve as targeting agents are anti-TAC, or other interleukin-2 receptor antibodies; 9.2.27 and NR-ML-05, reactive with the 250 kilodalton human melanoma-associated proteoglycan; and NR-LU-10, reactive with a pancarcinoma glycoprotein. An antibody targeting agent may be an intact (whole) molecule, a fragment thereof, or a functional equivalent thereof. Examples of antibody fragments are F(ab')2, –Fab', Fab and F[v] fragments, which may be produced by conventional methods or by genetic or protein engineering. Linkage is generally covalent and may be achieved by, for example, direct condensation or other reactions, or by way of bi- or multi-functional linkers. Within other embodiments, it may also be possible to target a polynucleotide encoding a modulating agent to a target tissue, thereby increasing the local concentration of modulating agent. Such targeting may be achieved using well known techniques, including retroviral and adenoviral infection.

For certain embodiments, it may be beneficial to also, or altematively, link a drug to a modulating agent. As used herein, the term "drug" refers to any bioactive agent intended for administration to a mammal to prevent or treat a disease or other undesirable condition. Drugs include hormones, growth factors proteins, peptides and other compounds. The use of certain specific drugs within the context of the present invention is discussed below.

Within certain aspects of the present invention, one or more modulating agents as described herein may be present within a pharmaceutical composition. A pharmaceutical composition comprises one or more modulating agents in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. One or more modulating agents (alone or in combination with a targeting agent and/or drug) may, but need not, be encapsulated within liposomes using well known technology. Compositions of the present invention may be formulated for any appropriate manner of administration, including for example, topical, oral, nasal, intravenous, intracranial, intraperitoneal, subcutaneous, or intramuscular administration.

A pharmaceutical composition may also, or alternatively, contain one or more drugs, which may be linked to a modulating agent or may be free within the composition. Virtually any drug may be administered in combination with a modulating agent as described herein, for a variety of purposes as described below. Examples of types of drugs that may be administered with a modulating agent include analgesics, anesthetics, antianginals, antifungals, antibiotics, anticancer drugs (e.g., taxol or mitomycin C), antiinflammatories (e.g., ibuprofen and indomethacin), anthelmintics, antidepressants, antidotes, antiemetics, antihistamines, antihypertensives, antimalarials. antimicrotubule agents (e.g., colchicine or vinca alkaloids), antimigraine agents, antimicrobials, antiphsychotics. antipyretics, antiseptics, anti-signaling agents (e.g., protein kinase C inhibitors or inhibitors of intracellular calcium mobilization), antiarthritics, antithrombin agents, antituberculotics, antitussives, antivirals, appetite suppressants, cardioactive drugs, chemical dependency drugs, cathartics, chemotherapeutic agents, coronary, cerebral or peripheral vasodilators, contraceptive agents, depressants, diuretics, expectorants, growth factors, hormonal agents; hypnotics, immunosuppression agents, narcotic antagonists, parasympathomimetics, sedatives, stimulants, sympathomimetics, toxins (e.g., cholera toxin), tranquilizers and urinary antiinfectives.

The compositions described herein may be administered as part of a sustained release formulation (i.e., a formulation such as a capsule or sponge that effects a slow release of modulating agent following administration). Such formulations may generally be prepared using well known technology and administered by, for example, oral, rectal or subcutaneous implantation, or by implantation at the desired target site. Sustained-release formulations may contain a modulating agent dispersed in a carrier matrix and/or contained within a reservoir surrounded by a rate controlling membrane (see, e.g., European Patent Application 710,491 A). Carriers for use within such formulations are biocompatible, and may also be biodegradable; preferably the formulation provides a relatively constant level of modulating agent release. The amount of modulating agent contained within a sustained release formulation depends upon the site of implantation, the rate and expected duration of release and the nature of the condition to be treated or prevented.

Pharmaceutical compositions of the present invention may be administered in a manner appropriate to the disease to be treated (or prevented). Appropriate dosages and a suitable duration and frequency of administration will be determined by such factors as the condition of the patient, the type and severity of the patient's disease and the method of administration. In general, an appropriate dosage and treatment regimen provides the modulating agent(s) in an amount sufficient to provide therapeutic and/or prophylactic benefit. Within particularly preferred embodiments of the invention, a modulating agent or pharmaceutical composition as described herein may be administered at a dosage ranging from 0.001 to 50 mg/kg body weight, preferably from 0.1 to 20 mg/kg, on a regimen of single or multiple daily doses. For topical administration, a cream typically comprises an amount of modulating agent ranging from 0.00001% to 1%, preferably 0.0001% to 0.002%. Fluid compositions typically contain about 10 ng/ml to 5 mg/ml, preferably from about 10 pg to 2 mg/mL modulating agent. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

Modulating Agent Methods of Use

In general, the modulating agents and compositions described herein may be used for stimulating β-catenin mediated gene transcription. Such stimulation may be performed in vitro and/or in vivo, preferably in a mammal such as a human. Within each of the methods described herein, one or more modulating agents may generally be administered alone, or within a pharmaceutical composition. In each specific method described herein, as noted above, a targeting agent may be employed to increase the local concentration of modulating agent at the target site.

β-catenin mediated gene transcription may be stimulated in any of a variety of contexts. As used herein, the phrase "β-catenin mediated gene transcription" refers to the transcription of any gene that increases in the presence of increased levels of cytosolic β-catenin. Such genes include, but are not limited to, genes that are activated by the Wnt-mediated signaling pathway, such as c-myc (see He et al., *Science* 281:1509–12, 1998).

Within certain aspects, the present invention provides methods for increasing the level of free β-catenin (i.e., β-catenin that is not complexed with α-catenin) in a cell. Such methods comprise the step of contacting a cell with a modulating agent as described herein. The step of contacting may be performed using any method that is suitable for the particular cell type. In vitro, for example contacting may be achieved by adding modulating agent to the growth medium. In vivo, contact may be achieved by administration, as described herein. For administration to skin cells, topical administration is generally preferred. Contact is performed using an amount of agent and for a sufficient duration to result in a detectable increase in the level of β-catenin in the cell. Such an increase may be detected directly (e.g., using immunohistochemical methods), or indirectly, based on a detection of cellular differentiation or changes in cadherin-mediated cell adhesion, as described herein.

Contact with a modulating agent as described above further results in enhanced activation of β-catenin mediated gene transcription in the cell. Such activation may be readily detected using any standard method for detecting changes in transcription, such as hybridization techniques and amplification techniques involving polymerase chain reaction (PCR). Alternatively, downstream effects of such transcription may be detected. Such downstream effects may include, but are not limited to, terminal differentiation and hair growth.

As noted above, contact of a cell with a modulating agent as described herein may stimulate terminal differentiation of the cell. Accordingly, the present invention provides methods for using a modulating agent to stimulate differentiation in a cell. Cells in which differentiation may be stimulated include, but are not limited to, skin cells, such as keratinocytes. Terminal differentiation may be detected by photographic methods, based on standard criteria that are well known in the art. For example, one sign of terminal differentiation is the loss of intermediate filament bundles.

Contact of a skin cell with a modulating agent may further stimulate hair growth. For such applications, administration is preferably achieved by direct contact with the scalp of the mammal (e.g., by topical application or cutaneous injection). Enhanced hair growth may be detected based on increased hair density and/or rate of growth.

It has been found, within the context of the present invention, that a modulating agent can induce keratinocytes to terminally differentiate into squams. Accordingly, a modulating agent may be used to cause the shedding (exfoliation) of old skin. For such uses, administration is preferably topical, with direct application to the skin of a mammal. Enhancement of exfoliation may be beneficial, for example, in plastic surgery, for improvement of photodamaged skin and for minimization of wrinkles. Such modulating agents may represent an improvement over harsh chemical exfoliants presently in use. Enhancement of exfoliation may generally be detected based on the appearance of new skin, which may be identified visually or using any of a variety of well known assays for detecting sloughing of skin cells.

A modulating agent may further be used to ameliorate hearing loss resulting from a variety of inner ear disorders, such as hyperacusis and tinnitus. Regeneration of hair cells of the inner ear, by contact with a modulating agent as described herein, may result in improvement in such ear disorders and lessened hearing loss.

The following Examples are offered by way of illustration and not by way of limitation.

EXAMPLES

Example 1

Preparation of Representative Modulating Agents

This Example illustrates the solid phase synthesis of representative peptide modulating agents.

The peptides were synthesized on a 431A Applied Biosystems peptide synthesizer using p-Hydroxymethylphenoxymethyl polystyrene (HMP) resin and standard Fmoc chemistry. After synthesis and deprotection, the peptides were de-salted on a Sephadex G-10 column and lyophilized. The peptides were analyzed for purity by analytical HPLC, and in each case a single peak was observed. Peptides were made as stock solutions at 10 to 25 mg/mL in dimethylsulfoxide (DMSO) or water and stored at −20° C. before use.

Representative peptides synthesized by this method are illustrated below (SEQ ID NOs: 4 and 5):

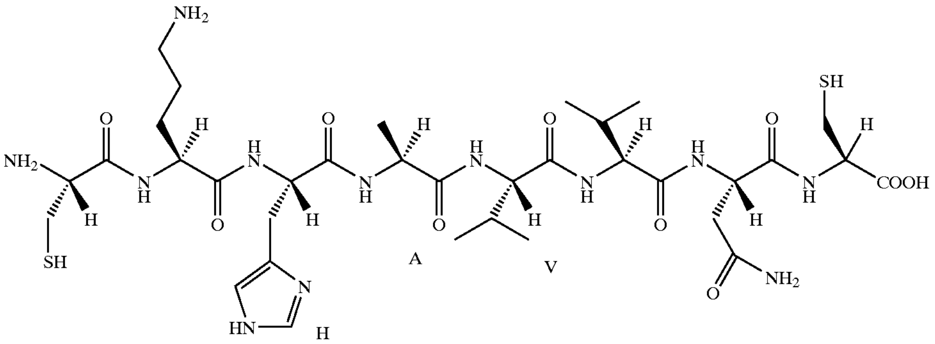

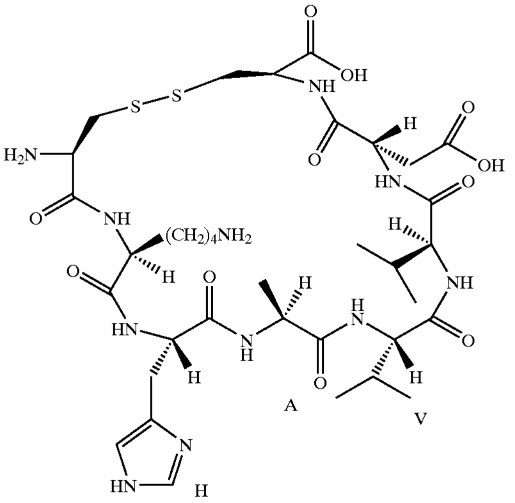

Example 2

Disruption of Interations between α-catenin and β-catenin

The Example illustrates the use of representative modulating agents to disrupt interations between α-catenin and β-catenin.

The linear peptide H-CKHAVVN-OH (SEQ ID NO:4; Example 1, upper structure) and the cyclic peptide H-CKHAVVNC-OH (SEQ ID NO:5; Example 1, lower structure) were synthesized using standard solid phase peptide synthesis techniques as described above. Both of these peptides contain the amino acid sequence HAV. In addition, the cyclic peptide has a disulfide tether, Ac-Cys-S-S-Cys-$NH_2$.

Figure 5:
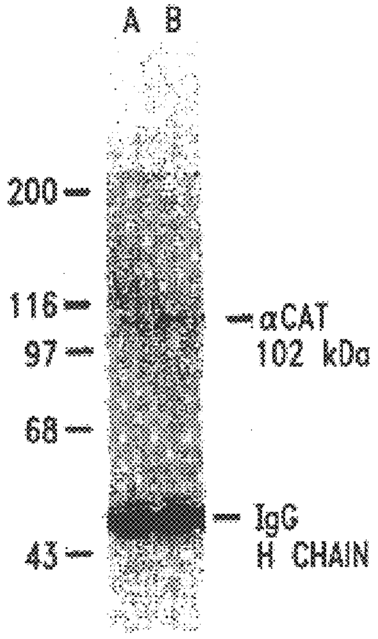
FIG. 5 is a Western blot of proteins immunoprecipitated from adult mouse brain extracts utilizing anti-β-catenin antibodies in the presence of either the representative modulating agent H-CKHAVVNC-OH (SEQ ID NO:4; Lane A) or the control peptide H-CKHGVVNC-OH (SEQ ID NO:6; Lane B) and probed with anti-α-catenin antibodies.

These peptides, as well as two control peptides (H-CKHGVVNC-OH, SEQ ID NO:6, and H-CKHGVVNC-OH, SEQ ID NO:51) were analyzed for their ability to disrupt α-catenin/β-catenin interactions, as judged by standard immunoprecipitation methods. FIG. 5 shows a Western blot of proteins immunoprecipitated from mouse brain extracts in the presence of either H-CKHAVVNC-OH (SEQ ID NO:4; lane A) or H-CKHGVVNC-OH (SEQ ID NO:6; lane B) and probed with anti-α-catenin antibodies. Brains from adult mice were homogenized in TC buffer (10 mM Tris pH 6.8 containing 1 mM $CaCl_2$, 500 μM phenylmethylsulfonylfluoride, 10 μg/ml leupeptin, 10 μg/ml aprotinin, and 5 μg/ml pepstatin) at wet weight to volume ratio of 1:2. Five-fold concentrated IP buffer (50 mM Tris pH 7.4 containing 750 mM NaCl, 5% Triton X-100, 2.5% NP-40) was then added to the homogenate at a volume to volume ratio of 1:4. The homogenate was then incubated with continuous agitation for 3 hours at 4° C. in the presence of either H-CKHAVVNC-OH (SEQ ID NO:4) or H-CKHGVVNC-OH (SEQ ID NO:6) at a concentration of 1 mg/ml. At the end of the incubation period, the homogenate was centrifuged (10,000×g) for 5 minutes at 4° C. Aliquots (50 μl) of the supernatant were incubated with 1.25 μg mouse monoclonal anti-μ-catenin antibody (Transduction Laboratories, Lexington, Ky.) with continuous agitation for 18 hours at 4° C. An aliquot (25 μl) of Protein G Sepharose (Pharmacia Biotech, Baie d'Urfe, Quebec) suspended in one-fold concentrated IP buffer containing 500 μM phenylmethylsulfonylfluoride, 10 μg/ml leupeptin, 10 μg/ml aprotinin, and 5 μg/ml pepstatin was added to each incubation mixture and the mixtures were incubated with continuous agitation for an additional 4 hours at 4° C. The mixtures were then centrifuged (5,000×g) for 5 minutes at 4° C. Immunoprecipitates were washed five times with one-fold concentrated IP buffer and resuspended in solubilization buffer (62.5 mM Tris pH6.8 containing 2% SDS, 10% glycerol, and 5% β-mercaptoethanol). The suspensions were heated at 100° C. for 5 minutes, and then subjected to SDS-PAGE. Following PAGE, the proteins were electrophoretically transferred to nitrocellulose membrane (0.22 μm pore size; Micron Separations Inc., Westboro, Mass.). The membrane was incubated for 1 hour in TTBS buffer (25 mM Tris pH 7.6, 0.1% Tween 20 and 0.9% w/v NaCl) containing 5% w/v dry skimmed milk, and then incubated for 1 hour in TTBS containing mouse anti-α-catenin antibodies (diluted 1:500; Transduction Laboratories, Lexington, Ky.). The membrane was washed 3 times with TTBS, and incubated for 45 minutes in TTBS containing goat anti-mouse IgG antibody conjugated to horseradish peroxidase (diluted 1:5000; Kirkegaard and Perry Laboratories, Gaithersburg, Md.). Finally, the membrane was washed 3 times with TTBS, and the immunoreactive proteins were detected using an enhanced chemiluminescence kit (ECL; Amersham Life Sciences Inc., Oakville, Ontario) and autoradiographic film (Fuji, Minami-Ashigara, Japan). Molecular mass markers (in kDa) are shown on the left-hand side of the blot. α-catenin (αCAT; molecular mass 102 kDa) is indicated on the right-hand side of the blot. Mouse immunoglobulin G was also immunoprecipitated. The mouse immunoglobulin G heavy chain (IgG H CHAIN) is indicated on the right-hand side of the blot.

Figure 6:
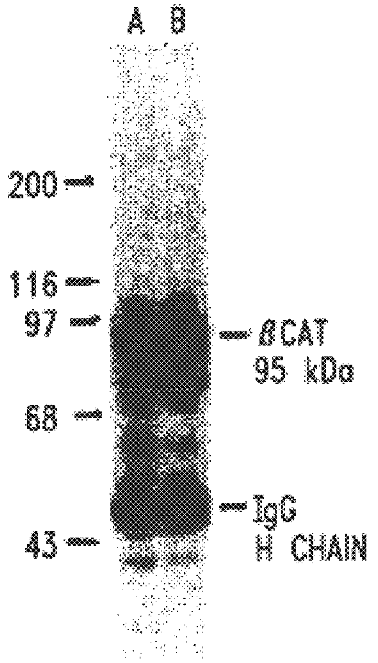
FIG. 6 is a Western blot as shown in FIG. 3, re-probed with anti-β-catenin antibodies.

The Western blot shown in FIG. 5 was stripped and re-probed with anti-β-catenin antibodies (diluted 1:500 in TTBS; Transduction Laboratories, Lexington, Ky.). FIG. 6 shows the Western blot which was probed with the β-catenin antibodies. Molecular mass markers (in kDa) are shown on the left-hand side of the blot. β-catenin (βCAT; molecular mass 95 kDa) is indicated on the right-hand side of the blot. Mouse immunoglobulin G was also immunoprecipitated. The mouse immunoglobulin G heavy chain (IgG H CHAIN) is indicated on the right-hand side of the blot.

Only the results obtained utilizing the linear peptides H-CKHAVVNC-OH(SEQ ID NO:4) and H-CKHGVVNC-OH (SEQ ID NO:6) are shown, as similar results were obtained using the cyclic peptides H-CKHAVVNC-OH (SEQ ID NO:5) and H-CKHGVVNC-OH (SEQ ID NO:51). In the presence of either linear or cyclic peptides containing the β-catenin HAV motif, α-catenin was immunoprecipitated to a lesser extent from the adult mouse brain extracts than in the presence of the control peptides. Therefore, both linear and cyclic peptides containing the HAV motif (amino acid sequences H-CKHAVVNC-OH (SEQ ID NO:4) and H-CKHAVVNC-OH (SEQ ID NO:5), respectively; FIG. 2) are capable of disrupting the interaction between α-catenin and β-catenin. None of the peptides affected the ability of the anti-β-catenin antibodies to immunoprecipitate β-catenin (molecular mass 95 kDa; FIG. 6).

Example 3

Disruption of Cell Adhesion

This Example illustrates the use of representative modulating agents to inhibit cadherin-mediated cell adhesion.

Three peptides (N-Ac-CKHAVVNC-$NH_2$, N-Ac-CKHGVVNC-$NH_2$, and H-KHAVVN-OH; SEQ ID NOS: 5, 51 and 8 respectively) were tested for their ability to disrupt cell adhesion. Normal human breast A1N4 cells were grown on gridded glass coverslips to approximately 30% confluence. Peptides were dissolved in distilled water at a concentration of 100 μg/ml. Each of the three peptide solutions was mixed 1:1 with a solution containing the fluorescent marker DAPI (Molecular Probes Inc: Eugene, Oreg.) dissolved in water at a concentration of 40 μg/ml. All of the mixtures were centrifuged at 10,000×g for 5 minutes immediately before use in the experiments. An aliquot (3 ml) of each peptide/DAPI mixture was taken up in an Eppendorff microinjection pipette. Microinjection was performed using an Eppendorf microinjector and micromanipulator coupled to an IM35 inverted Zeiss microscope with phase contrast and Hoffman optics. Cells to be injected were located and their position on the grid noted. For microinjection, the pipette was brought close to the cell layer and the micromanipulator programmed to return to the same plane. Cells were injected with 0.2 pL of peptide/DAPI mixture. This corresponds to approximately 1/100 of the cell volume and results in a final intracellular concentration of peptide of 0.5 mg/ml. The morphology of the injected cells was noted at hourly intervals. After 4 hours, a difference in the morphology of the cells injected with the various peptides was observed. Cells injected with the peptides N-Ac-CKHAVVNC-$NH_2$ (SEQ ID NO:5) and N-Ac-CKHGVVNC-$NH_2$ (SEQ ID NO:51) were indistinguishable from surrounding uninjected cells. In contrast, cells injected with the peptide H-KHAVVN-OH (SEQ ID NO:8) had become rounded, and they were detached from their neighbors. This result suggests that the peptide H-KHAVVN-OH (SEQ ID NO:8) is capable of disrupting the interaction between α-catenin and β-catenin, thus causing a disruption of cadherin-mediated cell adhesion. These results also indicate that protection of the C-terminus and N-terminus of a peptide renders the peptide inactive (compare the results for N-Ac-CKHAVVNC-$NH_2$ (SEQ ID NO:5) in this Example with H-CKHAVVNC-OH (SEQ ID NO:5) in Example 2).

Example 4

Modulating Agent Stimulation of Differentiation

This Example illustrates the use of representative modulating agents to stimulate terminal differentiation in keratinocytes.

Keratinocytes (Clonetics Corporation, Walkersville, Md.) were grown in keratinocyte growth medium (Clonetics) with 1 mm calcium. The cells were treated with the peptide modulating agent (KHAVVNRQIKIWPQNRRNKWKK; SEQ ID NO:72) at a concentration of 1 mg/ml medium for 48 hours. The medium was replaced after 24 hours with fresh medium containing fresh peptide. The cells were fixed and photographed after being exposed to the peptide for 48 hours.

Figure 7A:
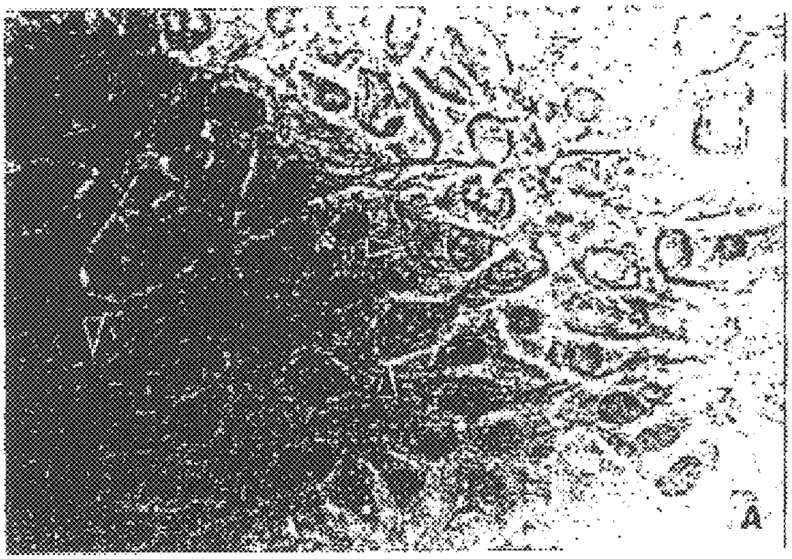
FIGS. 7A–7D are photographs illustrating the effect of a representative modulating agent on cultured keratinocytes.
Figure 7B:
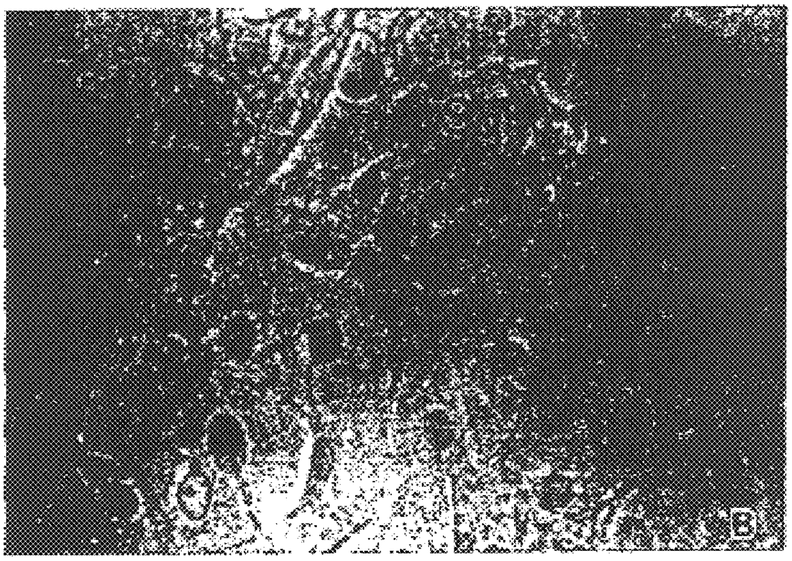
Figure 7C:
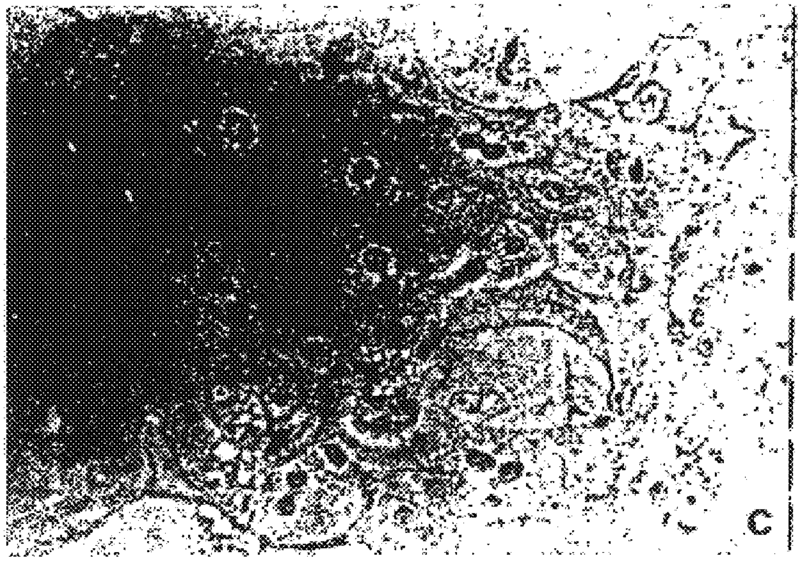
Figure 7D:
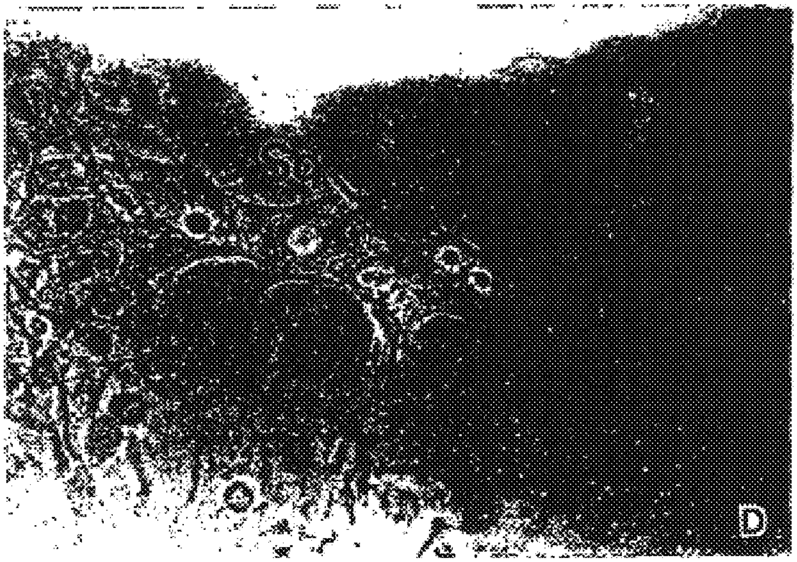

Representative photographs are shown in FIGS. 7A–7D. Untreated keratinocytes exhibited pronounced bundles of intermediate filaments (arrows) and did not form squams after 48 hours (FIG. 7A). Cells exposed to the peptide were much flatter and had lost intermediate filament bundles (FIGS. 7B to 7D). Many cells had partially detached from the substratum and formed a layer of terminally differentiated cells known as squams (labeled Sq in FIGS. 7B and 7D, shown by arrows in FIG. 7C). These data demonstrate that the modulating agents described herein, which disrupt interactions between β-catenin and α-catenin, stimulate β-catenin mediated gene transcription and cause keratinocytes to terminally differentiate into squams.

From the foregoing, it will be evident that although specific embodiments of the invention have been described herein for the purpose of illustrating the invention, various modifications may be made without deviating from the spirit and scope of the invention. Accordingly, the present invention is not limited except as by the appended claims.

What is claimed is:

1. A method for increasing the level of free β-catenin in a cell, comprising contacting a cell with a sufficient amount of a modulating agent effective to inhibit an interaction between α-catenin and β-catenin, wherein the agent comprises an internalization moiety and one or more of:

(a) the amino acid sequence Lys-His-Ala-Val-Val (SEQ ID NO:1); or (b) a peptide analogue or peptidomimetic of the amino acid sequence Lys-His-Ala-Val-Val (SEQ ID NO:1) that retains the ability to disrupt an interaction between α-catenin and β-catenin;

and thereby increasing the level of free β-catenin in the cell.

2. The method according to claim 1, wherein the modulating agent comprises the linear peptide sequence Lys-His-Ala-Val-Val (SEQ ID NO:1).

3. The method according to claim 2, wherein the modulating agent comprises a sequence selected from the group consisting of Lys-His-Ala-Val-Val-Asn (SEQ ID NO:8), Leu-Lys-His-Ala-Val-Val-Asn (SEQ ID NO:9), Leu-Lys-His-Ala-Val-Val (SEQ ID NO:10), Cys-Lys-His-Ala-Val-Val-Asn-Cys (SEQ ID NO:4), Cys-Leu-Lys-His-Ala-Val-Val-Asn-Cys (SEQ ID NO:12), Cys-Leu-Lys-His-Ala-Val-Val-Cys (SEQ ID NO:13) and Cys-Lys-His-Ala-Val-Val-Cys (SEQ ID NO:15).

4. The method according to claim 1, wherein the modulating agent comprises a cyclic peptide ring comprising the sequence Lys-His-Ala-Val-Val (SEQ ID NO:1).

5. The method according to claim 1, wherein the modulating agent comprises the amino acid sequence Lys-His-Ala-Val-Val (SEQ ID NO:1) in a linear or cyclic peptide ranging from 5 to 16 amino acid residues in length.

6. The method according to claim 1, wherein the internalization moiety is covalently linked to the amino acid sequence Lys-His-Ala-Val-Val (SEQ ID NO:1) or the peptide analogue or peptidomimetic of the amino acid sequence Lys-His-Ala-Val-Val (SEQ ID NO:1) of the modulating agent.

7. The method according to claim 6, wherein the internalization sequence comprises a sequence selected from the group consisting of Arg-Gln-Ile-Lys-Ile-Trp-Phe-Gln-Asn-Arg-Arg-Met-Lys-Trp-Lys-Lys (SEQ ID NO:47), Arg-Gln-Ile-Lys-Ile-Trp-Pro-Gln-Asn-Arg-Arg-Asn-Lys-Trp-Lys-Lys (SEQ ID NO:48) or Lys-Lys-Trp-Lys-Lys-Trp-Trp-Lys-Lys-Trp-Trp-Lys-Lys-Trp-Lys-Lys (SEQ ID NO:49).

8. The method according to claim 7, wherein the modulating agent has the sequence Lys-His-Ala-Val-Val-Asn-Arg-Gln-Ile-Lys-Ile-Trp-Pro-Gln-Asn-Arg-Arg-Asn-Lys-Trp-Lys-Lys (SEQ ID NO:72).

9. The method according to claim 1, wherein the internalization moiety is a liposome, and wherein the amino acid sequence Lys-His-Ala-Val-Val (SEQ ID NO:1) or the peptide analogue or peptidomimetic thereof is encapsulated within the liposome.

10. The method according to claim 1, wherein the internalization moiety is an antibody or ligand that specifically binds to a cell surface receptor.

11. The method according to claim 1, wherein the modulating agent is linked to a targeting agent.

12. The method according to claim 1, wherein the modulating agent is linked to a drug.

13. The method according to claim 1, wherein the modulating agent is present within a pharmaceutical composition comprising a pharmaceutically acceptable carrier.

14. The method according to claim 13, wherein the composition further comprises a drug.

15. The method according to claim 13, wherein the modulating agent is present within a sustained-release formulation.

16. The method according to claim 4, wherein the sequence within the cyclic peptide ring is selected from the group consisting of Cys-Lys-His-Ala-Val-Val-Asn-Cys (SEQ ID NO:5), Cys-Leu-Lys-His-Ala-Val-Val-Asn-Cys (SEQ ID NO:23), Cys-Leu-Lys-His-Ala-Val-Val-Cys (SEQ ID NO:24), Cys-Lys-His-Ala-Val-Val-Cys (SEQ ID NO:25), Lys-His-Ala-Val-Val-Asn-Asp (SEQ ID NO:26), Lys-His-Ala-Val-Val-Asn-Glu (SEQ ID NO:27), Lys-His-Ala-Val-Val-Asp (SEQ ID NO:28), and Lys-His-Ala-Val-Val-Glu (SEQ ID NO:29), wherein a disulfide bond is formed between the two cysteine residues in SEQ ID NOs:5, 23, 24, and 25, and an amide bond is formed between the N- and C-terminal amino acid residues in SEQ ID NOs: 26, 27, 28 and 29.

* * * * *